United States Patent
Tubbs et al.

(10) Patent No.: US 7,635,425 B2
(45) Date of Patent: Dec. 22, 2009

(54) INTEGRATED HIGH THROUGHPUT SYSTEM FOR THE ANALYSIS OF BIOMOLECULES

(75) Inventors: Kemmons A. Tubbs, Mesa, AZ (US); Karl F. Gruber, Tempe, AZ (US); Randall W. Nelson, Phoenix, AZ (US)

(73) Assignee: Intrinsic Bioprobes, Inc., Tempe, AZ (US)

( * ) Notice: Subject to any disclaimer, the term of this patent is extended or adjusted under 35 U.S.C. 154(b) by 288 days.

(21) Appl. No.: 11/843,826

(22) Filed: Aug. 23, 2007

(65) Prior Publication Data

US 2008/0181819 A1  Jul. 31, 2008

Related U.S. Application Data

(60) Division of application No. 11/462,933, filed on Aug. 7, 2006, now Pat. No. 7,311,826, which is a continuation of application No. 10/710,994, filed on Aug. 16, 2004, now Pat. No. 7,087,165, which is a division of application No. 10/053,098, filed on Jan. 15, 2002, now Pat. No. 6,783,672.

(60) Provisional application No. 60/262,530, filed on Jan. 18, 2001, provisional application No. 60/262,852, filed on Jan. 18, 2001.

(51) Int. Cl.
B01D 15/08 (2006.01)

(52) U.S. Cl. .................. 210/198.2; 210/502.1; 210/635; 210/656

(58) Field of Classification Search ................ 210/635, 210/656, 659, 198.2, 502.1; 96/101; 422/70, 422/100, 101
See application file for complete search history.

(56) References Cited

U.S. PATENT DOCUMENTS

| | | | | |
|---|---|---|---|---|
| 4,272,503 | A * | 6/1981 | Camin et al. | 424/1.49 |
| 4,772,691 | A * | 9/1988 | Herman | 536/24.3 |
| 5,171,537 | A * | 12/1992 | Wainwright et al. | 422/100 |
| 5,556,598 | A * | 9/1996 | Raybuck et al. | 422/100 |
| 5,997,746 | A * | 12/1999 | Valaskovic | 210/656 |
| 6,048,457 | A * | 4/2000 | Kopaciewicz et al. | 210/321.6 |
| 6,190,559 | B1 * | 2/2001 | Valaskovic | 210/656 |
| 6,200,474 | B1 * | 3/2001 | Kopaciewicz et al. | 210/321.6 |
| 6,416,716 | B1 * | 7/2002 | Shukla et al. | 422/101 |
| 6,498,039 | B2 * | 12/2002 | Nelson | 436/86 |
| 6,537,502 | B1 * | 3/2003 | Shukla et al. | 422/101 |
| 6,569,383 | B1 * | 5/2003 | Nelson et al. | 422/68.1 |

* cited by examiner

*Primary Examiner*—Ernest G Therkorn
(74) *Attorney, Agent, or Firm*—Snell & Wilmer L.L.P.

(57) ABSTRACT

Described is an affinity microcolumn comprising a high surface area material, which has high flow properties and a low dead volume, contained within a housing and having affinity reagents bound to the surface of the high surface area material that are either activated or activatable. The affinity reagents bound to the surface of the affinity microcolumn further comprise affinity receptors for the integration into high throughput analysis of biomolecules.

10 Claims, 21 Drawing Sheets

INTEGRATED HIGH THROUGHPUT SYSTEM FOR THE ANALYSIS OF BIOMOLECULES

CROSS-REFERENCE TO RELATED APPLICATIONS

This application is a divisional of U.S. patent application Ser. No. 11/462,933 and entitled "Integrated High Throughput System for the Analysis of Biomolecules" filed on Aug. 7, 2006, now U.S. Pat. No. 7,311,826, which is a continuation of U.S. patent application Ser. No. 10/710,994 and entitled "Integrated High Throughput System for the Analysis of Biomolecules" filed on Aug. 16, 2004, now U.S. Pat. No. 7,087,165, which is a divisional of U.S. patent application Ser. No. 10/053,098 and entitled "Integrated High Throughput System for the Mass Spectrometry of Biomolecules" filed on Jan. 15, 2002, now U.S. Pat. No. 6,783,672, which is a continuation-in-part of provisional applications 60/262,530 and 60/262,852, both filed on Jan. 18, 2001.

FIELD OF INVENTION

The present invention is related to the field of proteomics. More specifically, the present invention is a method and device for rapid identification and characterization of biomolecules recovered from biological media. Additionally, the present invention includes the ability to process numerous different samples simultaneously (high throughput analysis).

BACKGROUND OF THE INVENTION

Recent advances in human genome sequencing have propelled the biological sciences into several new and exciting arenas of investigation. One of these arenas, proteomics, is largely viewed as the next wave of concerted, worldwide biological research. Proteomics is the investigation of gene products (proteins), their various different forms and interacting partners and the dynamics (time) of their regulation and processing. In short, proteomics is the study of proteins as they function in their native environment with the overall intention of gaining a further, if not complete, understanding of their biological function. Such studies are essential in understanding such things as the mechanisms behind genetic disorders or the influences of drug mediated therapies, as well as potentially becoming the underlying foundation for further clinical and diagnostic analyses.

There are several challenges intrinsic to the analysis of proteins. First, and foremost, any protein considered relevant enough to be analyzed resides in vivo in a complex biological environment or media. The complexity of these biological media present a challenge in that, oftentimes, a protein of interest is present in the media at relatively low levels and is essentially masked from analysis by a large abundance of other biomolecules, e.g., proteins, nucleic acids, carbohydrates, lipids and the like. Technologies currently employed in proteomics are only able to overcome this fundamental problem by first fractionating the entire biological media using the relatively old technology of two-dimensional (2D) sodium dodecyl sulphate-polyacrylamide gel electrophoresis (SDS-PAGE), wherein numerous proteins are simultaneously migrated using a gel medium, in two dimensions as a function of isoelectric point and molecular size. In order to ensure migration in a predictable manner, the proteins are first reduced and denatured, a process that destroys the overall structures of the proteins and voids their functionality.

Present day state-of-the-art proteomics involves the identification of the proteins separated using 2D-PAGE. In this process, gel spots containing separated proteins are excised from the gel medium and treated with a high-specificity enzyme (most commonly trypsin) to fragment the proteins. The resulting fragments are then subjected to high-accuracy mass analysis using either electrospray ionization (ESI) or matrix-assisted laser desorption/ionization time-of-flight (MALDI-TOF) mass spectrometries (MS). The resulting data, in the form of absolute molecular weights of the fragments, and knowledge of the enzyme specificity are used in silico to search genomic or protein databases for information correlating to the empirical data on the fragments. Analytical methods and searching protocols, refined over the past seven years, have evolved to a point where only a few proteolytic fragments, determined with high mass accuracy, are needed to identify a gel-separated protein as being present in a certain gene.

However, identification of the gene producing a protein of interest is only the first step in the overall, much larger process of determining protein structure/functionality. Numerous questions that arise cannot be answered by the 2D-PAGE/MS approach. One major issue deals with the primary structure of the protein. During the commonly practiced identification process, at most, fifty percent of the protein sequence is viewed, leaving at least fifty percent of the protein unanalyzed. Given that potentially numerous splice variants, point mutations, and post-translational modifications exist for any given protein, many variants and modifications present within a protein will ultimately be missed during the identification process—many of which are responsible for disease states. As such, proteins are not viewed in the full structural detail needed to differentiate (normal) functional variants form (disease-causing) dysfunctional variants.

Furthermore, current identification processes make no provision for protein quantitation. Because many disease states are created or indicated by elevated or decreased levels of specific proteins and/or their variants, protein quantitation is a very important component of proteomics. Presently, protein quantitation from gels is performed using staining approaches that inherently have a relatively high degree of variability, and thus inaccuracy. The staining approaches can be replaced using isotope-coded affinity tags (ICAT) in conjunction with mass spectrometric quantification of proteolytic fragments generated from 2D-PAGE. However, the ICAT approach is still subjective to the aforementioned protein variants in that protein variants will yield mass-shifted proteolytic fragments that will not be included in the quantification process. Likewise, other approaches, such as ELISA (enzyme-linked immunosorbant assay) and RIA (radioimmunoassay), are equally subjected to the complications of quantifying a specific protein in the presence of its variants. Lacking the ability to resolve a target protein from its variants, these techniques will essentially monitor all protein variants as a single compound; a process that is oftentimes misleading in that a disease may be caused/indicated by elevated level of only a single variant, not the cumulative level of all the variants.

Moreover, the 2D-PAGE/MS approaches make no provision for exploring protein-ligand (e.g., other proteins, nucleic acids or compounds of biological relevance) interactions. Because denaturing conditions are used during protein separation, all protein-ligand interactions are disrupted, and thus are out of the realm of investigation using the identification approach. Separate other approaches focus specifically on the analysis of protein-ligand interactions. The most frequently used of these are the yeast two-hybrid (Y2H) and phage display approaches, which use in vivo molecular recognition events to trigger the expression of genes that produce reporter proteins indicating a biomolecular interaction, or selectively amplify high-affinity binding partners, respectively. Other instrumental approaches rely on biosensors utilizing universal physical properties or tags (e.g., surface plasmon resonance or fluorescence) as modes of detection. The two major limitations of these approaches is that they are generally slow and that interacting partners pulled from biological media are detected indirectly, yielding no specific or identifying information about the binding partner.

Lastly, none of the aforementioned approaches are favorable to large-scale, high-throughput analysis of specific proteins, their variants and their interacting partners in large populations of subjects. All of the aforementioned approaches require several hours (2D-PAGE) to several weeks (Y2H) to perform on a single sample. As such, time and, monetary expenses preclude application to the hundreds-to-thousands of samples (originating from hundreds-to-thousands of individuals) necessary in proteomic, clinical, and diagnostic applications.

To date, there are no universal, integrated systems capable of the high-throughput analysis of proteins for all of the aforementioned reasons. Thus, there exists a pressing need for new and novel technologies able to analyze native proteins present in their natural environment. Encompassed in these technologies are: 1) the ability to selectively retrieve and concentrate specific proteins from biological media for subsequent high-performance analyses, 2) the ability to quantify targeted proteins, 3) the ability to recognize variants of targeted proteins (e.g., splice variants, point mutations and post-translational modifications) and to elucidate their nature, 4) the capability to analyze for, and identify, ligands interacting with targeted proteins, and, 5) the potential for high-throughput screening of large populations of samples using a single, economical platform.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

SUMMARY OF THE INVENTION

It is an object of the present invention to provide an integrated system capable of selectively retrieving and concentrating specific biomolecules from biological media for subsequent high-performance analyses, quantifying targeted proteins, recognizing variants of targeted biomolecules (e.g., splice variants, point mutations and post-translational modifications) and elucidating their nature, analyzing for, and identifying, ligands interacting with targeted biomolecules, and high-throughput screening of large populations of samples using a single, unified, economical, multiplexed and parallel processing platform.

It is another embodiment of the present invention to provide an integrated system that comprises molecular traps, such as affinity microcolumns, derivatized mass spectrometer targets, mass spectrometers capable of multi-sample input and robotics with processing/data analysis interactive database software that accomplish the high throughput analysis.

It is yet another object of the present invention to provide individual components for the integrated system, such as molecular traps, derivatized targets and the like.

It is a further object of the present invention to provide a high throughput embodiment of the present invention that uses robotics for serial preparation and parallel processing of a large number of samples simultaneously.

It is yet a further object of the present invention to provide methods and processes for use of the individual components and the integrated system in biological applications.

It is still yet another object of the present invention to provide a device and method for the identification of point mutations and variants of analytes using an integrated system using high throughput analysis.

The novel features that are considered characteristic of the invention are set forth with particularity in the appended claims. The invention itself, however, both as to its structure and its operation together with the additional objects and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. § 112, paragraph 6 to define the invention. To the contrary, if the provisions of 35 U.S.C. § 112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

FIG. 7b is an expanded schematic illustration of the used station, which is comprised of microcolumn-integrated robotics having multiple positions for chemical modification, microcolumn functionalization, biological fluids analysis, transfer and the like.

DETAILED DESCRIPTION

Figure 1:
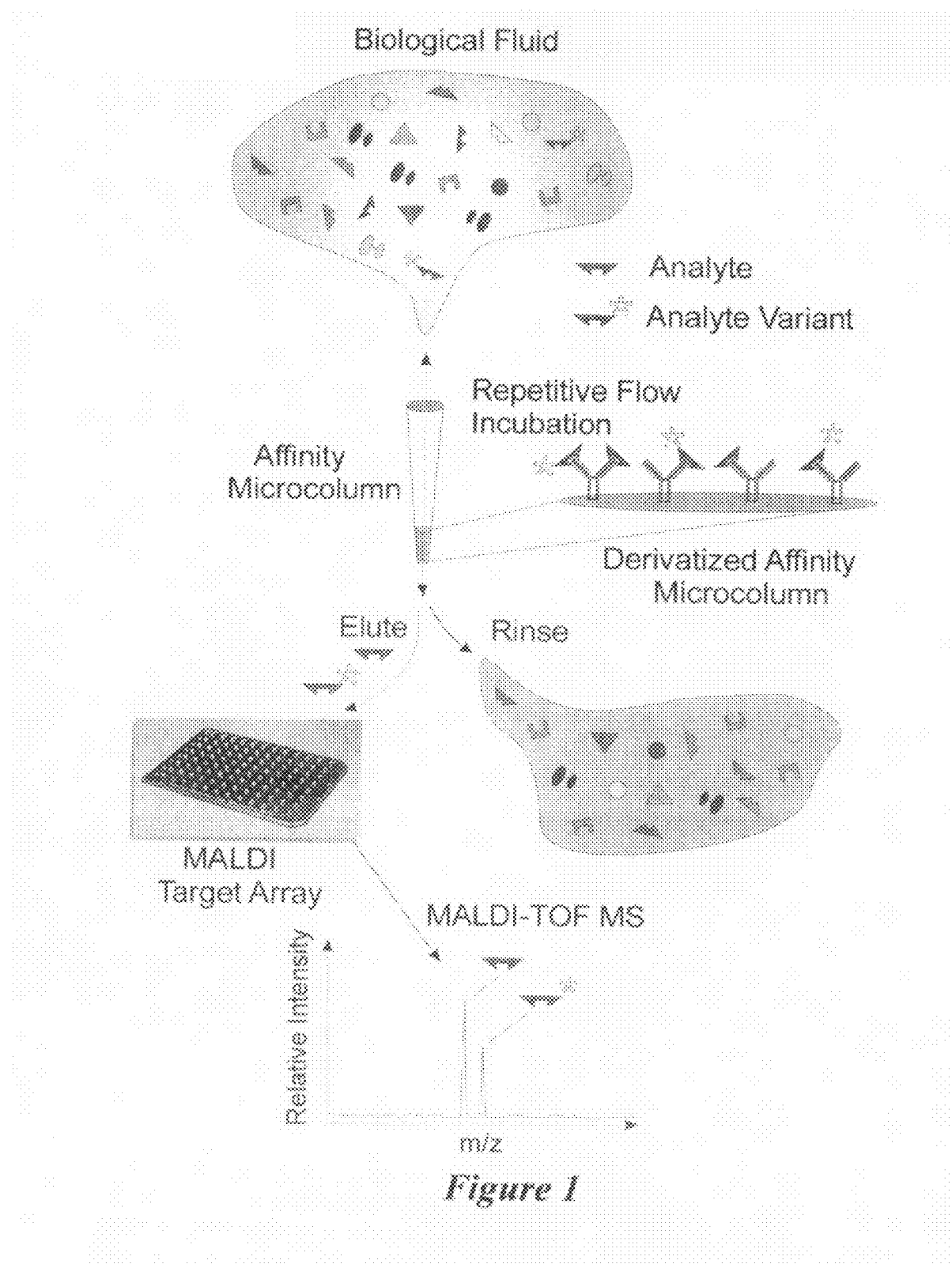
FIG. 1 is an illustration of the MSIA procedure. Analytes are selectively retrieved from solution by repetitive flow through a receptor-derivatized affinity pipette. Once washed of the non-specifically bound compounds, the retained species are eluted onto a mass spectrometer target or target array using a MALDI matrix (in the preferred embodiment). MALDI-TOF MS then follows, with analytes detected at precise m/z values. The analyses are qualitative by nature but can be made quantitative by incorporating mass-shifted variants of the analyte into the procedure for use as internal standards.

The present invention provides an integrated high throughput system capable of selectively retrieving and concentrating specific biomolecules from biological media for subsequent high-performance analyses, such as identification of biomolecules, quantifying targeted biomolecules, recognizing variants of targeted biomolecules (e.g., splice variants, point mutations and post-translational modifications) and elucidating their nature, such as analyzing for, and identifying, ligands interacting with the targeted biomolecules, and high-throughput screening of large populations of samples using a single, unified, economical, multiplexed and parallel processing platform.

The preferred embodiment of the integrated system comprises molecular traps, such as affinity microcolumns, processing stations, and derivatized mass spectrometer target arrays, which may be omitted in non-preferred embodiments, that work with mass spectrometers capable of single or multi-sample input and using processing/data analysis interactive databases. The present invention also includes methods and processes for use of the individual components and the integrated system in biological applications. Furthermore, the preferred embodiment of the present invention provides for the preparation and/or processing of multiple separate devices and/or samples to accomplish high throughput analysis.

A major component of the system of the present invention is the isolation or retrieval of specific analytes from their surrounding biological media in a biological sample. This is accomplished using a molecular trap. In a preferred embodiment of the molecular trap, the retrieval process entails repetitively flowing the biological sample through devices that have affinity receptors located on surfaces with a high surface area content. The affinity receptors are selected to capture specific analytes. In the high throughput embodiment, these molecular traps are formed into miniature columns, affinity microcolumns, thereby allowing numerous molecular traps to be located side-by-side and taking up minimal amount of physical volume. In a preferred form of the side-by-side embodiment, the numerous molecular traps are contained within a unitary component, such as a manifold or block of material. In this form the manifold contains numerous microchannels that house the molecular traps.

The molecular trapping process is accomplished by allowing sufficient physical contact between the affinity receptors located on the molecular traps and the analyte contained in the biological sample. The affinity receptors capture, or isolate, the specific analytes using an affinity interaction between the affinity receptors and the specific analytes. After the specific analytes are captured, residual or non-captured compounds are washed free of the molecular traps using a series of rinses. The capture and rinse processes result in the concentrating of the specific analytes into the low dead-volume of the affinity microcolumns.

After the specific analytes have been captured, they are eluted from the molecular traps using a small volume of a reagent capable of disrupting the affinity interaction. The eluted specific analytes are then stamped directly onto a mass spectrometry target platform for either mass spectrometry or for further processing, e.g., enzymatic/chemical modification via utilization of bioreactive MS target arrays, followed by subsequent preparation for mass spectrometry. Automated mass spectrometry then follows with either the specific analyte or modified fragments detected with high precision. Software capable of recognizing differences between samples, or from a standard, is used to aid in the analysis and organization into database of the large numbers of samples. Alternately, instead of stamping the eluted specific analytes onto a mass spectrometry target, the specific analytes may be eluted directly into an electrospray ionization mass spectrometer by using the molecular traps as a component in the sample introduction device, such as the needle of an electrospray mass spectrometer.

The high throughput embodiment of the present invention uses robotics for serial preparation and parallel processing of a large number of samples. The use of microcolumns in capturing the specific analytes enables an arrayed format, as mentioned above, that is ideal for such high-throughput processing since it minimizes the physical volume and/or area occupied by the microcolumn array. Use of affinity microcolumns with appropriately configured robotics allows multiple samples to be prepared, processed, start-to-finish, simultaneously on a unified platform thereby enabling high throughput of samples. Specifically, all capture, separation and elution steps are performed within the microcolumns managed by the robotics system or systems. This is in contrast to the use of other affinity capture methods (using, e.g., beaded media) where mechanical/physical means (e.g., centrifugation, magnetic or vacuum separation) are used to separate the specific analyte from the biological fluid and rinse buffers. Oftentimes this physical separation needs to be performed singularly, resulting in the disruption of a parallel processing sequence, as well as the ordering of the array. Because these mechanical/physical means are not necessary when using the microcolumns, parallel-processing sequences can be used without disruption and the integrity of an ordered spatial array is maintained throughout the entire process. Most conveniently, multiple preparations/analyses are performed serially and in parallel using robotics fitted to commonly used spatial arrays, e.g., 4-, 8-, 16-, 48-, 96-, 384 or 1536 well micro-titer plate formats.

Individual Components

Sample Modification/Preparation

In all of the below described embodiments, it may be desired that the biological media or the target analyte be modified or prepared either prior to affinity action or after affinity capture, but before elution onto a target or target array. Example modifications or preparations include, but are not limited to, reduction, labeling or tagging, in situ digests, partial on-surface digestion/modification, pH adjustments, and the like.

Molecular Traps

In one embodiment of the invention, molecular traps are microcolumnar devices that have bound affinity receptors. The molecular trap is chemically modified, such as by treatment with an amino-silanization reagent and subsequently activated for affinity receptor linkage using any one of a number of derivatization schemes. The use of affinity microcolumns overcomes the disadvantages entailed in performing affinity capture by other means. Specifically, affinity microcolumns, as described herein, are scaled to mass spectrometric analyses that have only become available in the last ten years. Prior to the advent of MALDI-TOF and ESI mass spectrometries, mass spectrometric analyses of polypeptides (if they could be performed at all) required amounts of analyte on the order of nanomoles, which, if isolated via affinity capture, required milliliter volumes of reagent containing bound receptors and, oftentimes, liter volumes of biological media. Given the low- to sub-femtomole sensitivities of MALDI-TOF and ESI mass spectrometries, the entire affinity isolation processes, including devices, can be scaled down by several orders of magnitude. Therefore, the affinity microcolumns described herein are devised and manufactured to fully utilize the sensitivity specifications of the recent enabling mass spectrometric techniques.

Figure 6:
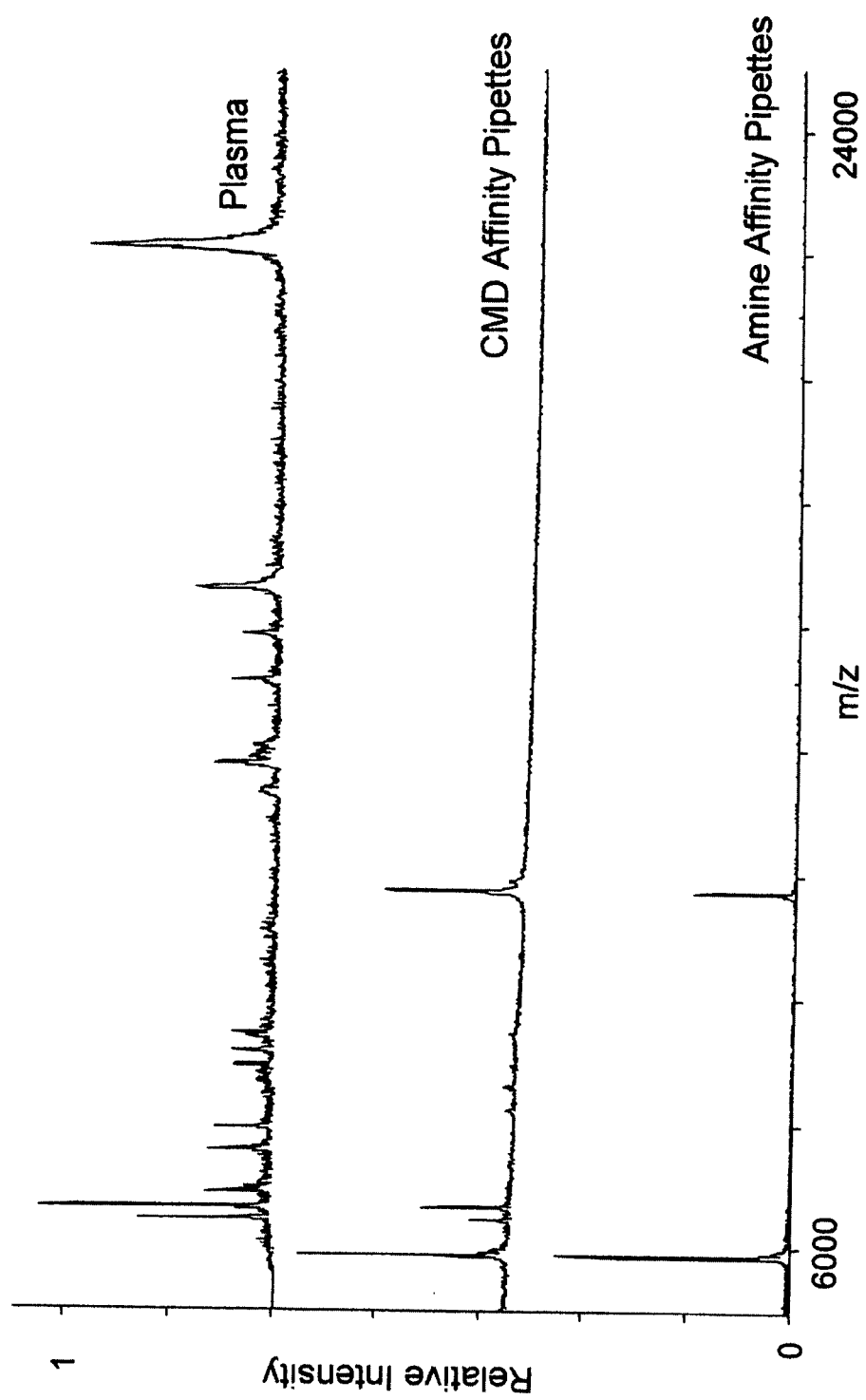
FIG. 6 Surface directed MSIA for defined biological fluid/$\beta_2$-microglobulin specificity. Use of polyclonal anti-$\beta_2$m affinity pipettes linked via carboxymethyl dextran amplification or amine base support chemistries enable differentiation of specifically bound versus non-specifically bound compounds during biological fluid/MSIA. Samples were prepared from biological fluid and used as in FIG. 2. (A) Human plasma. (B) Human plasma through CMD amplified $\beta_2$m affinity pipette. (C) Human plasma through amine/glutaraldehyde coupled $\beta_2$m affinity pipette. Direct analysis of human plasma spectra (top spectrum) lacks $\beta_2$m mass signature (MW$_{plasma}$=11734). CMD amplified affinity pipette chemistry target $\beta_2$m while exhibiting non-specifically bound compounds (middle spectrum). Only in the last case was $\beta_2$m efficiently retrieved from the biological fluid with low non-specifically bound compounds (bottom spectrum). This illustrates a preferred surface in the directed analysis of blood born biological fluid biomarkers using discreet affinity pipettes for specific mass detection.

An additional embodiment of the present invention is to provide a variety of affinity microcolumns specifically tailored to excel in a given biological media, illustrated in FIG. 6. Because all biological media are not exactly the same, with regard to biomolecule compositions and conditions, each affinity reagent derivatization scheme will behave differently in each biological media. For instance, affinity reagents tailored to retrieve a specific protein analyte present in plasma may not behave ideally when targeting the same analyte when present in a different biological media. Furthermore, the different buffer compositions and conditions of each biological media make available numerous small organic compounds that when retained and subsequently eluted with the targeted analyte will potentially deter from the mass spectrometric process. It is therefore necessary to construct affinity microcolumns for each biological fluid that show not only high specificity towards targeted analytes and low non-specific binding properties with regard to other large molecules that potentially interfere with the characterization of the analyte, but also exhibit minimal retention of smaller molecules that potentially interfere with the physical phenomena underlying mass spectrometric processes, e.g., MALDI or ESI.

Targets

After analytes are retrieved from biological media they are essentially microeluted and "stamped" directly from the affinity microcolumns onto a target or target array fitting into a mass spectrometer. In this manner, the spatial array from the initial multi-sample container, e.g., titer plate, is maintained throughout the affinity capture and washing steps, as well as onto the mass spectrometer target.

The present invention further embodies the use of specially tailored mass spectrometer targets in the automated preparation and analysis of proteins retrieved using the affinity microcolumns. Essential to incorporating the automated robotics into the high throughput, parallel process is reproducibility between each sample, and the ability to control the location of the samples upon deposition onto the mass spectrometer target. In order to ensure these aspects are instilled into the automated process, self-assembled monolayers (SAM) are patterned onto mass spectrometer targets in manners able to control the area of analyte deposition. For example, thiol or mercaptan compounds that are hydrophobic or hydrophillic in character are used to pattern contrasting areas on gold-plated targets. By surrounding a hydrophillic SAM with a hydrophobic SAM, a clear boundary is created that is able to confine aqueous sample (from the affinity microcolumns) to a clearly defined area on the target. The spatial array dictated by the parallel robotics can thus be maintained by simultaneously eluting multiple samples, from multiple affinity microcolumns (using robotics), onto a mass spectrometer target patterned to the same spatial array used in throughout the robotic processing.

In other applications, mass spectrometer targets are additionally tailored to include reactive surfaces capable of analyte processing. When investigating biomolecules using mass spectrometry it is often necessary to perform telltale chemistries and/or enzymologies to gain further detail on the structure of an analyte. Of particular importance are analyses that use specific chemical or enzymatic modifications in combination with mass spectrometry for purposes such as identifying analytes, analyte variants and modifications present within an analyte. Moreover, oftentimes it is of great value to quasi-purify mass spectrometric preparations by removal of potentially interfering species from solution through scavenging interactions designed to remove the interferences while leaving the target analyte available of analysis. A most efficient means of performing these operations is to use mass spectrometer targets that are derivatized with chemicals or enzymes for the particular processing function.

In a preferred embodiment, a target or target array is made by first etching channels around designated target areas using photoresist technologies. A layer of gold is deposited onto the etched substrate, such as by traditional electro-plating techniques or plasma deposition. This layer of gold naturally follows the surface contours created by the etching. Depending upon the substrate, one or more intermediate layers may be required, such as a nickel intermediate layer is required when depositing a surface layer of gold. An activated or activatable reagent, capable of forming a chemical bond or adsorbing to the modified substrate surface, such as dithiobis (succinimidylproprionate) (DSP) or derivatives thereof, is then bound onto the target areas, but not elsewhere. Any transport solvent is either allowed to evaporate or removed producing a dry self-assembled monolayer (SAM) of the activated or activatable reagent. A protective layer is deposited onto the target SAM, such as dextran solubilized in appropriate solvent. When that solvent is DMSO, the DMSO is then removed by placing the target in a vacuum. The target (array) is then coated with a hydrophobic reagent, such as octadecyl mercaptan solubilized in a solvent that does not dissolve the protective layer. When dextran is the protective layer, isopropanol may be used to solubilize the hydrophobic reagent. The target is rinsed to remove any non-bound hydrophobic reagent. In the example where activated reagent is bound to the target areas, the activated reagent is made available for use by merely removing the protective layer, which also removes any hydrophobic reagent present in or on the protective layer, such as by rinsing with DMSO. In the example where activatable reagent is bound to the target areas, the reagent may be activated for use by either removing the protective layer followed by reagent activation using an activating reagent or by direct activation, where the solvent transporting the activating reagent also serves to dissolve the protective layer. In the second case, the dissolved protective layer is then removed by subsequent rinses. Finally, a bioreagent or biological reagent, such as a polymer, protein, peptide, or enzyme, is bound to the surface of the target areas. The binding of the bioreagent is facilitated by the activated reagent already bound to the target areas. In the case where there is activated reagent coated by the protective layer, the bioreagent may be added to the surface by either removing the protective layer and then adding bioreagent to the target area or by direct binding, where the solvent transporting the bioreagent also serves to dissolve the protective layer.

An advantage to the above target or target array manufacturing process is that the targets, once coated with the protective layer, may be stored for extended periods of time and then used at the discretion of the consumer. Another advantage of the target array is to provide a confined reaction surface for analyte processing and manipulation of impurities.

In yet another similar embodiment, mass spectrometer target surface or surfaces are derivatized with chemicals found to enhance sample preparation through promoting the formation of crystals of matrices used in the practice of MALDI. Such matrix crystal "seeding" is found invaluable in the automation of the entire sample preparation process, enabling the production of highly reproducible samples over the entire area of the target.

High Throughput Machine

The individual components described herein come together to form a single, integrated system capable of high-throughput analysis of analytes retrieved from biological media. Fundamental analyses begin with verifying the primary structure, i.e., sequence of analytes. Oftentimes, a single high-accuracy determination of molecular weight is sufficient to verify the primary structure of analytes. If higher precision is required in verifying the primary structure of an analyte, it is convenient to mass map the analyte (after retrieval) using chemically/enzymatically active mass spectrometer targets. During such mapping procedures, an analyte is digested using high specificity cleavage reagents to produce a multitude of signals when analyzed using mass spectrometry. When viewed as a group, these signals are able to verify primary structure with greater precision and redundancy than a single mass determination. Alternatively, these data can be used to search databases for variants of an analyte that differ largely from that predicted for a normal analyte, e.g., splice variants.

In a similar embodiment, other variants of analytes are mapped to elucidate the nature, location and origin of the variation. Analytes and variants present in a single sample are co-extracted from biological media using a common affinity reagent localized in the microcolumn and are simultaneously subjected to mapping on an activated mass spectrometer target or target array. Because most analyte variants will share a large degree of homology with the normal analyte, most mapping signals will be common between the analyte and variant. However, uncommon, or mass-shifted, signals will also be present within the mapping data. Using these differential data, in combination with knowledge of the cleavage agent and information of the primary, tertiary, quanternary structures of the normal analyte, it is possible to elucidate the site of the variation. Furthermore, using knowledge of mass differences between component residues of the analyte (e.g., mass difference between amino acids in proteins or nucleic acids in DNA/RNA) and accurate determination of the mass-shifts, it is possible to determine the transposition that created the variant. Such analyses are of great value in elucidating, e.g., point mutations present in proteins or polymorphisms present in nucleic acids. Likewise, knowledge of molecular weights of potential modifying groups (e.g., glycans, phosphates, methyl, formyl and the like) can be used in combination with mapping data to elucidate the sites and nature of chemical modifications of the analyte. Finally, reactive targets designed to address specific modifications can be used in the integrated system for the determination of the quantity (number) of modifying moieties by cleaving them from the analyte and viewing subsequent mass shifts in mass spectra.

In another embodiment, the present invention is used in the high-throughput quantitation of specific analytes present in biological media. Using this process, analytes and internal references (analyte-like species) are simultaneously retrieved from biological media and processed through to mass spectrometry. In the same parallel processing operation, standard samples are analyzed to produce working curves equating analyte signal with the amount of analyte present in the biological media. The amount of analyte present in each sample can then be either judged as elevated relative to other samples, or determined absolutely using the working curve.

In a further embodiment, the present invention is used in determining the interacting partners involved in protein-ligand interactions. Essentially, affinity microcolumns are derivatized with ligands of interest with the intention of screening biological media for interacting partners. The ligands act as affinity receptors capable of selectively isolating analytes from the biological media. Once isolated, the analytes are subjected to mass spectrometry for identification. Oftentimes, direct mass spectrometric analysis, and a knowledge of components present in the biological media, is sufficient to identify retained analytes via direct molecular weight determination. Alternatively, unknown analytes are subjected to digestion using chemically/enzymatically active targets and the resulting fragments (e.g., proteolytic fragments) subjected to mass spectrometry. The accurately determined molecular weights of the fragments (and knowledge of cleavage specificity) are then used to fuel genomic or protein database searches capable of identifying the analytes.

In a similar embodiment, protein-ligand interactions are investigated by designing an affinity reagent to target a specific protein that in itself retains other analytes. In this manner, protein complexes are retrieved from biological media by targeting one of their constituents. Using the aforementioned analytical approaches, the identity and nature of the components of the complex are then delineated.

Specific embodiments in accordance with the present inventions will now be described in detail. These examples are intended to be illustrative, and the invention is not limited to the materials, methods or apparatus set forth in these embodiments.

EXAMPLES

Affinity Microcolumn Manufacture

Below are described the directed formation of the preferred embodiments of biologically sensitive affinity-ligated microcolumns capable of high through-put via efficient affinity capture, release and rapid, sensitive and accurate mass spectrometric analysis of specific or non-specifically targeted analytes. The below examples describe numerous approaches, architectures and device deliveries to provide stable configurations in biological rich environments.

Example 1

Porous Glass Molecular Trap Preparation Using Metal Mold-Graphite Spray Release

Porous glass molecular traps are metered to the specifications of commercially available wide-bore P-200 pipettor tips using annealing molds made of stainless steel (100-1000 holes of 0.071 inch (entrance) per mold; 2-degree taper, polished and treated with graphite release agent). The molds are loaded with soda lime glass spherical beads (150-200 μm; 75% $SiO_2$, 15% $Na_2O$ and 10% CaO), and annealing is achieved in an argon-backfilled furnace by ramping the temperature from 772° C. (equilibrated, t=0) to 800° C. (t=3 minutes; one-minute equilibration). Upon completion of the ramp-anneal, the molds are immediately removed from the oven and the porous glass molecular traps extracted from the molds. This process typically yields porous glass molecular traps with high-flow characteristics and appropriate bore and taper to fit the entrance of the wide-bore P-200 pipette tips (room temperature porous glass molecular traps dimensions: 0.061 in. (entrance), 0.092 in. (length), 2-degree taper).

In a preferred embodiment, the molecular traps are then inserted into the top of the pipette tip and allowed to locate to the bottom section (narrow section). The molecular traps are seated by the application of a sufficient amount of pressure applied from the top. The pipette tip may be heated prior insertion of the molecular trap to aid in the seating process.

Sample mass spectra using an affinity microcolumn prepared according to this example are illustrated in FIG. 2-5.

Example 2

Porous Glass Molecular Trap Manufacture Using Ceramic Molds

Pyrex

Ceramic molds are described to manufacture porous Pyrex glass molecular traps. Porous glass molecular traps are metered to the specifications of commercially available wide-bore P-200 pipettor tips using ceramic annealing molds. Zircar type-R plates (four by six by one-quarter inches) were purchase from Zircar Corporation (Florida, NY) and were end-mill surfaced for maximum flatness and CNC machined (2100 holes, 0.0625 inch bottom cut, 2-degree taper). Four of the ceramic molds loaded with ball-milled powdered borosilicate "Pyrex" (size ranging from 4 μm to 300 μm; 81% $SiO_2$, 4% $Na_2O$, 0.5% $K_2O$, 13% $B_2O_3$ and 2% $Al_2O_3$), were stacked in a furnace where they underwent initial temperature equilibration, using a slow temperature up-ramp (60 minutes) to below the Pyrex softening point (816° C.). The molds were then equilibrated for thirty minutes prior to being ramped to about the Pyrex softening point (821° C.), which was then maintained for about thirty minutes to form porous glass molecular traps. For concerted heat treatment (using enhanced silica glass); the molds were down-ramped to 708° C. where they were maintained for 2 to 20 hours (depending on the amount of etching desired) prior to a slow final temperature ramp down for removal. When immediate use is required, the molds are slowly temperature down-ramped to a reasonable retrieval temperature (generally 300° C.) to avoid glass cracking. This process typically yields porous Pyrex glass molecular traps with high-flow characteristics and appropriate bore and taper to fit the entrance of the wide-bore P-200 pipette tips (room temperature porous glass molecular traps dimensions: 0.0625 in. (entrance), 0.130 in. (length), 2-degree taper).

Example 3

Porous Silica Glass Molecular Trap Manufacture Using Ceramic Molds

Vycor

The ceramic molds described in EXAMPLE 2 are used to manufacture porous Vycor glass molecular traps. Zircar type-R ceramic molds were loaded with powdered "Vycor" (Corning Corporation), porous Vycor (Corning Corporation), controlled porous glass (Controlled Porous Glass, Inc., NJ), (size ranging from 4 μm to 300 μm, depending upon desired flow-through characteristics; 96% $SiO_2$), and were stacked in a furnace where they underwent initial temperature equilibration, using a slow temperature up-ramp (90 minutes) to below the Vycor softening point (1500° C.), they are then equilibrated for thirty minutes prior to being ramped up to about the Vycor softening point (1530° C.), which was maintained to form porous glass molecular traps. The molds were slowly temperature down-ramped to a reasonable retrieval temperature (generally about 300° C.) to avoid glass cracking. This process typically yields porous Vycor glass molecular traps with high-flow characteristics and appropriate bore and taper to fit the entrance of the wide-bore P-200 pipette tips.

Example 4

Porous Silica Molecular Trap Manufacture Using Ceramic Molds

Silica Gel or Fused Silica

The ceramic molds described in EXAMPLE 2 are used to manufacture porous glass molecular traps using silica gel or fused silica. Zircar type-R ceramic molds were loaded with powdered porous silica gel (Sigma Chemical Company) or fused silica (Corning Corporation) (sizes ranging from 4 μm to 300 μm depending upon desired flow-through characteristics; 100% $SiO_2$), and were stacked in a furnace where they underwent initial temperature equilibration, using a slow temperature up-ramp (90 minutes) to below the silica softening point (1550° C.) where they are equilibrated for thirty minutes prior to being ramped to about the silica softening point (1585° C.), which is then maintained to form porous silica molecular traps. The molds were slowly temperature down-ramped to a reasonable retrieval temperature (generally about 300° C.) to avoid silica cracking, This process typically yields porous silica molecular traps with high-flow characteristics and appropriate bore and taper to fit the entrance of the wide-bore P-200 pipette tips.

Example 5

Etched Porous Silica Molecular Traps

Hyper-porous porous silica molecular traps formation is accomplished by exposing porous silica molecular traps formed in Example 4 to various electrochemical etching conditions. For example, porous silica molecular traps are placed in a solution of aqueous HF (25-50%) in absolute ethanol while applying an etching current (120-200 mA/cm$^2$) and irradiation (150 mW/cm$^2$) for one to twenty minutes thereby creating porous silicon hydride surfaces.

Example 6

Porous Powdered Metal Molecular Trap Manufacture Using Metal Mold

Porous metal molecular traps are metered to the specifications of commercially available wide-bore P-200 pipettor tips. A metal mold is machined, having either a reverse incline (relative to the previous molds, i.e., narrow at the top) or the same directional taper, and containing a slight raised lip (for required overfill) around the openings located at the bottom of the mold (for porous powdered metal exit by a pushpin). The mold rests upon a removable bottom plate, is loaded with powdered metal (e.g., brass, copper, silver, gold), and pressure (commensurate to form individual welds between metal particles) is applied to the throated/raised powdered metal surface via an Arbor press equipped with a complementary push-pin for each hole. After the powdered metal molecular traps are formed, the bottom plate is removed, and a pushpin is applied to the narrow end of the hole to release the porous powdered metal molecular trap from the mold. Porous powdered metal molecular traps are oven annealed to enhance architectural stability and form metal oxides for organo-functionalization.

It should be recognized that the molecular traps may be made from a variety of different materials and or different combinations of different materials and still fall within the scope of the present invention. The only limiting requirement is that the materials must be able to bind affinity reagents, or chemically modified to bind affinity reagents, to their surfaces. The most preferred materials or combinations of materials have high surface areas or are capable of being modified to have high surface areas.

While the above examples utilize a tapered profile for the microcolumns, non-tapered or shapes, such as cylindrical columns, may be used and still fall within the scope of the present invention. In deed, for high throughput embodiments, the non-tapered form is preferred since the taper slows the manufacturing process.

Chemical Activation of the Molecular Traps

Example 7

Silane Coating/Functionalization of Porous Glass Molecular Traps

Porous molecular traps formed via EXAMPLES 1-6, or other equivalent processes, may undergo pretreatment conditioning combining various water, mineral acid treatments, and concomitant water rinses and drying prior to chemical derivatization (silanization). For example, porous glass molecular traps are leached by suspending them in distilled or purified water (generally ten fold by volume) under elevated temperatures (typically below the boiling point of water) with orbital shaking or 1 to 24 hours, with (or without) two to three change outs of fresh water. All water is then removed and two subsequent acid treatments applied. First, 1N hydrochloric acid in water is applied (ten fold) over the porous glass molecular traps, at elevated temperatures a time, such as one to two hours, and water rinsed until a neutral (or near neutral) pH is obtained. Second, 1N nitric acid in water is carried out as performed with the first acid treatment. The porous glass molecular traps are dried either at room temperature or in a vacuum oven (100° C., 1 atm, overnight).

The dried/pretreated porous glass molecular traps are then chemically activated, such as by coating them with a silanating reagent, e.g. 10% silanating agent, ca. N-[3-(trimethoxysily)propyl]ethylenediamine, in anhydrous toluene under reflux with orbital shaking overnight, to produce functionalized porous molecular traps. The silane coated porous molecular traps are allowed to cool to room temperature, rinsed in methanol under reflux, followed by room temperature rinses, until the supernatant is negative to ninhydrin and/or trinitrobenzoic acid (tnbs) analysis. Other, useful silanating reagents include, but are not limited to, 3-(trimethoxysily)propyl acrylate, 3-(trimethoxysily)propyl amine, N-[3-(trimethoxysily)propyl]aniline, N1-[3-(trimethoxysily)propyl]diethylenetriamine, N-[3-(trimethoxysily)propyl]ethylenediamine, 3-(trimethoxysily)propyl methacrylate, [3-(trimethoxysily)propyl] octadecyldimethlammonium chloride, N-[3-(trimethoxysily) propyl]polyethylenimine, N1-[3-(trimethoxysily)propyl] carboxylic acid, aminopropyltriethoxysilane, 3-glycidoxypropyltrimethoxysilane, thiolpropyltrimethoxysilane, chloropropyltrimethoxysilane, octadecyltrimethoxysilane, octadecyltrichlorosilan, O-[2-(trimethoxysilyl) ethyl] O'-methylpolyethylene glycol, silyl aldehyde, and the like.

These reactions may be accentuated by base catalysis, such as using triethylamine (TEA) added to the reactions or by performing them under pressure by applied vacuum (ca. 1 atm).

Microcolumn Housing (Pipette) Manufacture

In the preferred embodiment, where non-tapered molecular traps are used, micropipettes, which are used as the microcolumn housing are modified as follows:

Microcolumn housings, such as micropipette tips are formed, such as by injection molding or other means well known in the arts. The distal ends of the housings are modified from ordinary micropipettes by providing at least one inset projection, such as a ledge. In one embodiment, the projection is a continuous ledge that following the inner diameter of the distal end of the housing. However, in a more preferred embodiment the at least one inset projection is a single tang or triangular projection, more preferably, three tangs, and even more preferably six tangs. Thus, when the molecular traps are loaded into the housing, each rests upon the at least one inset projection. After the molecular traps are loaded into the housings, a portion of the sides of the housing directly adjacent to the molecular traps are crimped inward to a degree where there is slight frictional contact with the molecular traps. Care must be taken not to over crimp since that would destroy the contained molecular traps. In a preferred embodiment, the crimping is accomplished by heating the outer surface of the housing while cooling the contained molecular trap with a flow of cool gas (an inert gas is preferred). The heated housing is then forced inward using a gradual taper in the beating mold, thereby crimping the housing to the molecular traps.

Batch Functionality

Example 8

Batch Direct Activation/Derivatization of Functionalized Porous Molecular Traps

Direct batch activation/derivatization of microcolumns targets any reactive chemical group that will couple to the representative affinity ligand and provide an environmentally stable linkage. Batch activation/derivation approaches proceed in a myriad of ways, targeting activation/conjugation chemistries for biological modification with either organic and inorganic reagents, for example: primary amines, carboxylic acids, thiol groups, sulfhydryls hydroxyls, allyl groups, azides, aldehydes, hydrazides, maleimides; triazine and the like, that can be activated with homobifunctional, heterofunctional or polymeric reagents.

The instant example illustrates one of these approaches by incorporating glutaraldehyde activation followed by ligand coupling through primary amine groups with aldehyde groups on the glutaraldehyde-porous molecular trap. First, amine functionalized molecular traps are coupled to glutaraldehye (a 25% solution in 0.10 M sodium phosphate, pH 7.8, 100 mM NaCl buffer) using sodium cyanobohydride (10 mg/mL) mediated coupling (reaction times ranging from an hour to overnight). After several rinses with the phosphate buffer, the activated aldehyde groups on the glutaraldehyde matrix are incubated with the ligand of interest, such as a protein antibody. Uncoupled (excess) ligand is removed by extensive rinsing with HBS buffer (10 mM HEPES pH 7.4, 0.15 M NaCl, 0.005% Surfactant P20). This derivatization process yields molecular traps with a high analyte binding capacity. The molecular traps are then packed into the P-200 pipettor tips.

Example 9

Batch Amine Activation, Amplification, Reactivation and Derivatization of Functionalized Porous Molecular Traps

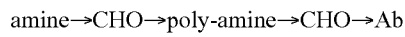

Microcolumn activation with amplification allows another approach for addressable ligand coupling. To create an amplified amine surface, mid to high-molecular weight amine-polymers, such as polylysine, aminodextran or amine modified starburst dendrimers, are cross-linked to the functionalized/activated porous molecular traps surface through a variety of appropriate chemistries. A glutaraldehyde activated amine microcolumn is incubated with polylysine in a sodium cyanoborohydrate mediated coupling. This polyamine microcolumn is then re-activated using glutaraldehyde, water rinsed and protein ligand conjugated.

Example 10

Damping of Nonspecific Binding via Batch Surface Amine Modification Activation/Derivatization of Functionalized Porous Molecular Traps

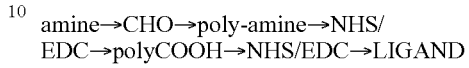

Another approach to ligand immobilization is through coupling of ligand-borne carboxyl groups to surface amines. An opportune way of creating an amplified amine surface is through cross-linking high-molecular weight polylysine, aminodextran, amine modified starburst dendrimer or polyacrylhydrazide to the functionalized porous molecular traps surface followed by distal carboxyl generation through a variety of chemistries, such as EDC-mediated linkage of carboxyl-terminated cross-linkers (e.g. succinic or glutaric anhydride) or bisoxirane activation (resulting in an epoxide-activated surface). These carboxyl microcolumns are then used to immobilize low-pI protein ligands via ca., EDC/NHS-mediated activation/coupling. Specifically, polylysine microcolumns are incubated in bulk in succinic (or glutaric) anhydride (100 mg/mL anhydride in 0.2M sodium acetate pH 4-5) with the reaction allowed to proceed to completion (i.e., negative tnbs and ninhydrin amine testing) generally for two to four hours, while pH is maintained by dilute hydrochloric acid addition. The carboxy microcolumns are then activated with 100 mM NHS and 100 mM EDC in water for 10-20 minutes at room temperature, water rinsed and a slight vacuum is applied prior to protein ligand coupling (antibody 1-10 mg/mL HBS buffer pH 7.5, overnight 4° C., shaker).

Example 11

Batch Polymer Modified Carboxylic Acid Activation/Derivatization of Functionalized Porous Molecular Traps Another approach involves surface amplification with water-soluble carboxyl containing polymers (carboxymethyl dextrans, carboxymethyl agaroses, carboxymethyl celluloses, carboxymethylamylose, polyglutamic acid, poly acrylic acids, carboxyl modified starburst dendrimers) like carboxymethyl dextran, followed by coupling of ligands, such as via interaction of primary amine groups with the carboxyl groups on the dextran matrix. First, the amine functionalized microcolumns are coupled to 15 kDa carboxymethyl dextran (CMD) executed in 100 mM sodium phosphate, pH 4.8, 100 mM NaCl buffer, via EDC (1-ethyl-3-(3-dimethylaminopropyl) carbodiimide) mediated coupling. After several rinses with the phosphate buffer, the carboxyl groups on the dextran matrix are activated with a mixture of EDC/N-hydroxy succinimide (NHS; 100 mM each, in $H_2O$) and incubated with the ligand of interest, such as a protein antibody. Uncoupled (excess) antibody is removed by extensive rinsing with HBS buffer (10 mM HEPES pH 7.4, 0.15 M NaCl, 0.005% Surfactant P20), after which the molecular traps are packed into the P-200 pipettor tips. This derivatization process yields microcolumns with a higher binding capacity, compared to microcolumns for which no amplification layer (the CMD matrix) is used. Although the initial amino-silation activation step results in amine surfaces (de facto a "functional surface"), it is preferred to amplify the surface in order to increase distance off the binding surface, loading capacity, and ensure a uniform (homogeneous) surface coating throughout the entire microcolumn (thereby reducing potential interactions that may occur with the glass substrate and result in non-specific binding).

Example 12

Batch Carboxymethyl Dextran Carbonyldiimidizaole (CDI) Activation/Derivatization of Functionalized Porous Molecular Traps In yet another approach to ligand immobilization, the EDC/NHS activation procedure of the CMD layer is replaced by an activation with N,N'-carbonyl diimidazole (CDI). This activation results in carboxyl and hydroxyl groups present in the CMD being converted to an imidazoyl carbamate intermediate capable of reacting with primary amines or sulfhydryls present in the affinity ligands. For instance, CMD microcolumns are rinsed with acetone followed by dimethylsulfoxide (DMSO). A 100 mg/mL solution of CDI in DMSO is then overlain above the CMD microcolumns, a vacuum applied, and the activation allowed to proceed from two hours to overnight on an orbital shaker. The CDI activated affinity pipettes are extensively rinsed in DMSO followed by acetone to form a CDT-activated CMD microcolumn. Importantly, the CDI-activated media is known to be reasonably stable, with shelf lives on the order of months given proper storage conditions (i.e., (wet) isopropanol or (dry) inert gas or vacuum). Thus, the CDI can act as a stable activator of the microcolumns and increase the longevity for pre-activated supply. Alternatively, the CDT-activated matrix is incubated with the protein antibody of interest. Uncoupled (excess) antibody is removed by extensive rinsing with HBS buffer (10 mM HEPES pH 7.4, 0.15 M NaCl, 0.005% Surfactant P20), after which the molecular traps are packed into the P-200 pipettor tips.

Example 13

Batch In-Situ Polymerization or Co-Polymerization via Surface Polymerization of Organo Functionalized Porous Glass Molecular Trap In this example, organo-functionalized porous glass molecular traps (c.a., methacryltrimethoxysilanated) are in-situ polymerized via free radical initiation. Typical co-polymerization monomers used include but are not limited to allyl dextran, allylamine allyl glycidyl ether, acrylic acid, and vinyldimethyl azlactone which can incorporate cross-linking agents, such as methylene-bis(acrylamine), using typical initiating reagents such as tetramethylenediamine (TEMED) or N,N,N',N'-tetramethyl-1,2-diaminoethane and ammonium persulfate in water. The degree of cross-linking and polymer size is controlled by amount of initiator, polymerization time, and available monomers for termination. This surface reaction results in functional groups abounding within the polymeric matrix, which covers the molecular trap surface. These groups are then available for activation/conjugation to ligands or subjected to additional activation and amplification prior to activation and ligand coupling.

Example 14

Metal Chelator Modified Porous Glass Molecular Traps

The incorporation of metal chelators into porous glass molecular trap is useful for metal binding biomolecule retrieval. Amine or polyamine microcolumns, prepared as in previous examples, are overlain in 0.1M phosphate at pH 7 and evacuated using a rotary evaporater. Primary amine surfaces are then directly coupled to bifunctional chelating agents such as ethylenediaminetetraacetic dianhydride (EDTA-DA), and diethylenetriaminepentaacetic dianhydride (DTPA-DA) at 20-100 mg/mL to form metal-chelating arms (TED and EDTA respectibly) able to bind tightly metals in a coordination complex for biomolecule trapping.

Alternatively, metal-chelators such as ethylenediaminetetaphosphoric acid (EDTPA), 1,4,7,10-tetracyclononane-N,N',N"-triacetic acid (NOTA), 1,4,7,10-tetraacacyclododecane-N,N',N",N'''-tetracetic acid (DOTA), 1,4,8,11-tetraazacyclotetradecane-N,N',N",N'''-tetraacetic acid (TETA), 1,2-bis(2-aminophenoxy)ethane-N,N,N'N' tetraacetic acid (BAPTA), N,N(biscarboxymethyl) L-lysine are solution activated using for instance NHS/EDC (100 mM each, 0.1 M phosphate, pH 7) mediation to couple carboxyl groups to localized surface primary amines.

Example 15

Formation of Biomimic Ligands, Preparation of Batch Dye-Functionalized Porous Glass Molecular Traps Synthetic dyes are useful affinity ligands by virtue of their reactivity with a wide variety of biological materials. Reactive dyes encompassing but not limited to triazine dyes (i.e., reactive black, reactive blues, reactive browns, reactive greens, reactive oranges, reactive reds, reactive yellows, etc.), for instance, have been linked to amino-microcolumns using a simple approach. The triazine dye of interest, ca. Cibacron Blue at 50 mg/mL dissolved in distilled water, is added to amino microcolumns in a round bottom flask and allowed to react overnight under low reflux. After ligand coupling, the biomimic microcolumns are rinsed with water and incubated with 1N salt solution under low reflux for thirty minutes. After extensive water rinses, the biomimic microcolumns are dried either in air or under vacuum at 90° C.

Example 16

Formation of Ion Exchange-Functionalized Porous Glass Molecular Traps in Batch

The incorporation of ion exchange media into porous glass molecular trap is useful for bio-molecule binding, retrieval and analysis or in sample cleanup as in desalting surfactant (SDS removal). In this instance, the amine or polyamine microcolumns, are activated targeting for example carbohydrate hydroxyl groups contained within dextran ion exchange media (e.g., dextran-sulfate, diethylaminoethyl-dextran (DEAE-dextran), heparin-sulfate, carboxymethyl dextran (generation described previously in EXAMPLE 10). Primary amine surfaces are activated with bifunctional (or activating) agents such as triazine, diglycidoxyether (oxiranines or epoxides) prior to dextran ion exchange carrier coupling. Likewise epoxide-functionalized microcolumns generated from initial silylanization reactions or via co-polymerization are used for derivatization.

Alternatively, amine microcolumns are incubated/coupled to activated dextran carriers. A further example is the use of aldehyde groups on dextran carriers generated by sodium meta periodate oxidation of dextran (vicinal diols) ion exchange carriers. Specifically, dextran ion exchange media (10-100 mg/mL) is incubated in the dark in 1M sodium meta periodate (in water), for two hours after which, the oxidized dextran ion exchange media is either precipitated in organic (ethanol/ether) or dialyzed in water overnight. Oxidized dextran ion exchange media is then incubated with amine or polyamine microcolumns (0.1 M phosphate, pH 7.5).

Example 17

Protein Immobilization to Microcolumns

Proteins with specific binding properties have specialized uses as receptors and ligands in immuno-chemistry. These affinity proteins include but are not limited to protein A, protein G, avidin and streptavidin reagents. Protein ligands, specifically protein A or G, are incorporated into porous glass molecular traps, for distal constant region (Fc) antibody capture or capture/conjugation with subsequent cross-linking prior to use as biomolecule retrieval agents. Avidin/biotin systems are used as alternative tethering agents which when coupled to antibody or analyte create conjugated agents with not only strong binding properties but with an amplified motif.

For example, amine or polyamine microcolumns, prepared as in previous examples, are overlain in 0.1M phosphate at pH 7 and evacuated using a rotary evaporator. Primary amine surfaces are then glutaraldhyde activated (25%, 4 to 24 hours), rinsed, and directly coupled to functional protein agents (or amine or hydrazide modified biotin) (1-10 mg/mL in HBS-EP) in a sodium cyanoborohydride (0.1 mg/mL) mediated coupling.

Example 18

Protein Modification/Digestion Using Microcolumns

Biomolecules with specific modifying or digestion properties are used as receptors and ligands in biochemistry. These biomolecules include, but are not limited to, proteins, peptides, enzymes, catalytic antibodies, and the like.

For example, trypsin modified microcolumn is prepared as in previous examples. When activated, the trypsin will make specific digests at either arginine or lysine points in amino acid sequences of proteins, such as a targeted analyte protein.

Alternately, other receptors may be used to synergized two biomolecules into a single entity, such as phosphorilization of an analyte by immobilized kinase.

Target Manufacture

The current target designs used by the commercial manufactures do not adequately support the rigorous and consistent use of arrayed and/or bioreactive targets. It is of great importance for these targets to achieve a high degree of inter-sample reproducibility.

There are at least three targets designs capable of correcting the problems encountered using the current design targets. These designs are as follows:

Targets Utilizing Plateaus

In a first embodiment of targets according to the present invention, there are "matched set" targets wherein a volume of analyte can be applied to a strictly defined area without the worry of spreading beyond the active area of the target, Volumes of analyte will meniscus on the top of a plateau formed by the target and, if correctly designed, will not seep down the sides of the plateau. Because of this meniscus action, the analyte will generally be in an aliquot volume of ~2-3 µL. This volume will fully cover the ~4 mm$^2$ area of the target completely, with little concern of overrunning the enzymatically-active area. Erratic digestion due to exposing the analyte to varying amounts of enzyme is therefore eliminated by fully covering (only) the active surface of the target. In addition, the ~2-3 µL volume will not evaporate if the targets are placed in an appropriately humidified incubator. Erratic digestion because of sample drying is therefore eliminated by maintaining the constant sample volume on the plateau.

In manufacture, there are plateaus milled into metal-base targets that fit into a larger (stainless steel) target that is ultimately introduced into the instrument. The height of the plateaus is determined empirically, with the criteria of finding the minimum height necessary to avoid analyte spreading. A height of ~0.5 millimeter is usually adequate; a height that can be easily introduced into the acceleration region of all MALDI-TOF instruments (minimum clearance ~2 mm). The overall dimensions of the plateaus are such to adequately confine analyte without introducing instrumental artifacts into the analysis.

A second embodiment uses thin-gauge metal targets that fit into the instruments via a tongue-in-groove design. Because of the thin gauge of the targets, and the necessity of having a grooved mounting bracket, it is impractical to mill (machine) these targets. Therefore, a press method is used (pressing the targets from the backside) to create the plateaus. Note, the pressing method requires the machining of an appropriate die.

The appropriate base material is determined empirically for compatibility with solvents used during manufacture, gold-coating properties and vacuum compatibility. Initially, base targets are made of polystyrene, which is compatible with manufacturing solvents, can be sputter-coated with high uniformity and has low out-gassing properties. However, other polymeric materials may be used. An advantage of the polymer-based targets is that they can be manufactured in large quantity at little expense.

The criteria for success with this type of target is to determine an optimum plateau geometry that: 1) adequately confines sample volumes to an exact surface area, 2) does not detract from the performance of the instrument, and 3) is easy and cost-effective to mass-produce.

Hydrophobic/Hydrophilic Contrast of Targets or Target Arrays

A second embodiment design for high-reproducibility bioreactive targets is to contrast enzymatically active sites with a hydrophobic media capable of confining the analytical volume to only the active area. In this approach, the enzyme is immobilized to gold/DSP/enzyme spots located on top of a generally hydrophobic target. The simplest way to manufacture the contrast devices is to construct them out of a hydrophobic material such as Teflon. Gold sample areas are placed on the target by a masking/sputter-coat process. The gold areas are then derivatized using our normal activation/immobilization methods. One concern regarding the Teflon device is that of surface charging in the mass spectrometer. Such effects (charging of the sample stage by removal of ions) are always a concern in mass spectrometry design. MALDI-TOF analyses have been done from sample targets made of non-conducting materials (e.g., quartz targets or gels) with only minor effects due to sample charging. These effects are even further minimized using the delayed-extraction methods available on all commercial MALDI-TOF instrumentation. However, any perturbations to mass spectrometer performance due to the targets may be eliminated by such methods as including electrical linking of the enzymatically-active surfaces in the masking/gold-coating process.

Another possibility for contrast devices is to derivatize metal-base targets to create a hydrophobic surface onto which hydrophilic enzymatically-active areas are constructed. Manufacturing protocols for this approach are more involved than the previous approach. It is necessary to follow a multi-step protocol to first coat the target with the hydrophobic media and then gold-coat a pattern of sample spots onto the hydrophobic coat using a masking process. The process involves: 1) Sputter coating of entire targets with gold, 2) Activation with DSP (if necessary), 3) Immobilization of hydrophobic compound, 4) Re-sputter target using pattern mask, and 5) Activate fresh gold and immobilize enzymes. An example using this process is to gold-coat a target and derivatize with 1-octadecanethiol (skip DSP activation). This process has been used to create C-18 derivatized surfaces. These surfaces are highly-hydrophobic as can be readily observed by beading of water. Once the target is derivatized with hydrophobic compound, a pattern of fresh gold is applied by masking and sputter-coating. The fresh gold is then activated and derivatized using e.g., the DSP/dextran/enzyme immobilization procedure. The process results in hydrophilic, enzymatically-activated spots surrounded by a hydrophobic media. To enhance visual contrast between active and hydrophobic areas, hydrophobic dyes containing a single primary amine and no other chemically-reactive group (e.g., Fast Violet B, Methylene Violet 3RAX) can be used in place of the C-18 layer. Likewise, other classes of dyes or chromaphoric hydrophobic compounds can be used to create more visual contrast between activated and hydrophobic areas of the targets. In preferred embodiment, hydrophillic mecaptoundecanoic acid dissolved in isopropanol is flash micro-deposited onto the arrayed targets, dried, and covered with octadecyl mercaptan rapidly forming contrasted target arrays. Contrasting can be reversed for hydrophobic analytes, or any combination thereof, including mixed SAM applications.

The criteria for success with this type of target is to find general derivatization methods (for high contrast targets) that are not too labor intensive or costly to prohibit large-scale manufacture.

Individual Targets (Inserts)

A third target embodiment design is that of using individual areas (inserts) that after digestion can be inserted into a base that fits into the commercial mass spectrometers. This approach emulates the "matched set" targets described above. The inserts will be of either plateau or contrast design, and will be economical to derivatize using higher cost enzymes (by using smaller volumes of higher concentration reagents). These targets (even when derivatized with low-cost enzymes) are very economical in terms of cost in research applications where they can be used one at a time.

The necessary limitation for success with this type of target is to construct "matched set" design targets as inserts fitting into the targets accepted by commercial instrumentation.

Biochips, and Small Array Targets

Another embodiment of the target arrays is incorporating bioreactive surfaces into/onto existing chip-based bioanalytical platforms. Micro-channel devices (chips) are now used in protein analysis and are ideal platforms for biomolecular separation (in one dimension) followed by enzymatic processing (by driving separated biomolecule in a second dimension over an enzymatically-active area) and MALDI-TOF analysis directly from the chip.

Other Active Surfaces, Derivatization Methods and Assays

Amplifying Media

In an another alternate embodiment surface amplifying media are used to increase the activity of the target array or the enzymatically-active targets. An example amplification is performed using solution based polymeric amplification techniques, either single step activated couplings, or in situ induced polymerization events. These modified surfaces display definite charge differences using either carboxylic acid or amine amplifying reagents (which are in themselves either activated or activatable).

General Enzyme Immobilization Kits

A significant product according to the present invention is a fully-activated General Enzyme Immobilization Kit The kits are comprised of a number of affinity micro-pipettes containing affinity microcolumns, activated or activatable targets or target arrays (whether amplified or not), and pre-made buffers. The purpose of the kits is to have the end-user derivatize targets in-house using proprietary enzymes, thereby eliminating shipment of reagents to the manufacturer for immobilization.

Ion-Exchange Surfaces

In still yet another embodiment, the targets or target arrays may be derivatized with carboxymethyl dextran (CMD) capable of a cation exchange process, which ultimately leads to higher quality MALDI-TOF spectra during the analysis of proteins in the presence of sodiated and potassiated buffers. Using the CMD targets, unwanted cations are scavenged from solution and replaced with protons or ammonium ions, dependent on which cation is used to pre-charge the targets.

Cation Exchange (CE) Targets

The value of CE surfaces has already been described; reduction of unwanted cations in buffer solutions to reduced signal heterogeneity thereby increasing mass spectral sensitivity (homogenization of signal). Reduction of alkali cations, using the CE surfaces, is also capable of improving matrix homogeneity during sample preparation. These attributes are of benefit to the MALDI-TOF analysis of both protein and nucleic acids. In one embodiment of a CE surface uses amplified surfaces of 500 kDa CMD. The 500 kDa CMD is chosen because of a higher exchange capacity than lower molecular weight CMD. It is estimated that approximately 10 picomole of CMD can be immobilized to the surface of a 4 $mm^2$ target. Considering that each strand of CMD will have ~1,000 valence sites for exchange (~30% of monomeric dextran converted to CMD), an exchange capacity of 10 nanomole is estimated for the targets, equating to a 1 μL aliquot of 10 mM alkali salt. However, the exchange properties of the CMD targets will have to be evaluated to determine the overall effectiveness in sample clean up. They are effective in alkali metal removal using a short single stranded DNA molecular (e.g., $d(T)_8$) mixed in the presence varying concentrations (0.1-10 mM) of buffer salts. DNA is chosen for the test assay because of the high propensity to retain alkali metals as counterions to the negatively charge phosphate backbone.

Using standard CMD targets it is likely to reach an exchange limit below the buffer concentration ranges used in a number of biological applications. Stronger CE functionalities (e.g., sulfonate groups created by treatment of dextran with chlorosulfonic acid) and methods capable of greater surface amplification (application of polymeric resins to create macroscopic (10-100 micrometer surfaces) may be used in order to raise the exchange capacity of the targets to a level capable of reducing deleterious effects experienced during the analysis of biomolecules present in moderate-high strength buffers.

Anion Exchange (AF) Targets or Target Arrays

Anion exchange targets or target arrays are a still further embodiment useful in sample cleanup by scavenging various anionic detergents from solution. Specifically, the presence of sodium dodecylsulfate (SDS) in protein solutions has always been of concern during MALDI-TOF analyses. SDS is generally disruptive of the crystal formation required for most of the MALDI matrices to function, and therefore needs to be removed from solution as part of sample preparation. Another anion that possibly has a deleterious effect on the MALDI process is phosphate ion.

Polylysine-amplified surfaces have intrinsically weak anion exchange properties. They are used in anion scavenging by analyzing test mixtures comprised of 5 different proteins in the presence of various concentrations of SDS. Polylysine surfaces may not provide the exchange capacity or strength needed to scavenge SDS from solution at relevant concentrations (10's of millimolar). Diethylaminoethyl (DEAE) exchange groups may be used as a replacement for the polylysine. Three derivatization schemes creating DEAE are possible. The first possibility is to link diethylaminoethylamine to 500 kDa CMD using EDC-mediated chemistry or CDI-activation. A necessary limitation to this approach is need for complete saturation of the carboxylic acid groups with DEAE. If all groups are not converted to DEAE, the surface will have (unpredictable) characteristics of both the cation and anion functionalities. A second method will be to activate polylysine surfaces using 1,5-difluoro-2,4-dinitrobenzene and link the DEAE to the surface through the benzylhalide. This has been done successfully using the 1,5-difluoro-2,4-dinitrobenzene method for selectively immobilizing peptides via their N-terminus. A possible downfall of this method, however, is the potential of severely cross-linking polylysine during the activation step, essentially making the surface inert to further derivatization. A third chemistry is to link diethylaminoethylamine to surfaces amplified with CDT-activated dextran. This method is a variation of the CDI-CMD derivatization, and should reduce heterogeneous cation/anion exchange properties, as well as have a significant exchange capacity. All of these preparation methods have been tried and assayed using test peptide mixtures in the presence of SDS. Enzymes, assays, incubator Enzymes Another embodiment uses combinations of biomolecules to accomplish combined multifunctional operations. Combined profiling, for example, uses two enzymes, such as endoproteases in combination with alkaline phosphatase, capable of mapping and subsequent dephosphorylation of biomolecules. Such an application is of value when elucidating the specific phosphorylation sites present in e.g., regulation proteins. The immobilization of the phosphatases with various endoproteases is accomplished with the ultimate goal of generating surfaces capable of pH-dependent operation. Activity can be gauged by assaying small phosphopeptides available from commercial suppliers.

Yet another embodiment uses snake venom phosphodiesterase (PD). Through partial sequencing, targets successfully derivatized with PD will add an extra dimension of specificity of PCR-based primer extension methods used in the analysis of short DNA fragments containing mutations present in DNA micro-satellites. The immobilization of PD to bioreactive targets may be accomplished, by gauging activity using small oligonucleotides. Studies involving both AP and PD relies on the general derivatization protocols according to the present invention.

Incubator

A common occurrence during proteolytic digestion using bioreactive targets in combination with the affinity microcolumns is the tendency of the sample to dry out (on the target or target array) during the course of digestion. A modified oven/incubator capable of performing digests over a range of temperatures (25-60° C.) has been constructed that surrounds the bioreactive targets in a constant humidity environment. Digests have been performed for times greater than one-hour using this incubator with little loss in sample volume. The devices is small and portable (dimensions: 4"×6"×1"; wt. ~0.5 lbs.; 120 V), operates at a single temperature (40° C.—sufficient for most applications of the bioreactive array), capable of maintaining a sample volume of 1-2 µL for times as long as one-hour using "matched set" targets, and amenable to use with robotic stations.

Biomolecular Applications

Example 18

Beta-2-Microglubulin ($\beta_2$M) Analysis from Urine

Porous glass molecular traps, manufactured according to example 1 above, were activated and derivatized in batches (30-50 per batch) prior to packing into the pipettor tips forming an affinity pipette. After acid conditioning (with 0.05 M HCl for 1-hour, air-dried), the porous glass molecular traps were treated with 10% amino-propyl triethoxysilane (Aldrich, Milwaukee, Wis.) in anhydrous toluene for 12-under reflux. The amine-functionalized porous glass molecular traps were then equilibrated in reaction buffer (100 mM sodium phosphate, pH 4.8, 100 mM NaCl) for 15 minute in a reaction vessel under slight vacuum. After equilibration, the buffer was replaced with a mixture of 15 kDa molecular mass carboxylated dextran (CMD, Fluka, Milwaukee, Wis.) and 1-ethyl-3-(3-dimethylaminopropyl) carbodiimide (EDC, Sigma, St. Louis, Mo.) (10 mg/mL each in the reaction buffer) and the air was again evacuated from the reaction vessel. The reaction was allowed to proceed for 1 hour (with two subsequent additions of EDC to the reaction mixture at ~20 and 40 minutes into the reaction) before terminating and rinsing. Prior to coupling of the antibody, the CMD-amplified porous glass molecular traps were rinsed vigorously with 100 mM sodium phosphate, pH 8.0, 0.5 M NaCl. The porous glass molecular traps were then activated for 10-minutes with EDC/N-hydroxy succinimide (NHS, Sigma, St. Louis, Mo.) (100 mM each, in H20) and incubated with the affinity purified rabbit anti-human $\beta_2$m IgG (DAKO, Carpinteria, Calif.) (0.1 mg/mL, in 20 mM sodium acetate, pH 4.7). Uncoupled antibody was removed by extensive rinsing with HBS buffer (10 mM HEPES pH 7.4, 0.15 M NaCl, 0.005% Surfactant P20). This manufacturing process yielded affinity pipettes with a binding capacity estimated at 10-100 pmol, while having a dead volume of approximately 1.5 µL. The anti-$\beta_2$m affinity pipettes were found to be stable and active for a period of at least three-months following antibody immobilization (by storing at 4° C. in HBS buffer).

Biological Fluids

All fluids were obtained immediately prior to use; protease inhibitor cocktail (PIC, Protease Inhibitor Cocktail Set III, Calbiochem, La Jolla, Calif.) was added immediately in order to minimize possible proteolytic degradation of $\beta_2$m.

Tears. Human tears were collected by washing the eye with doubly-distilled water (ddH$_2$O) and collecting the rinse. A 20 µL aliquot of the eye rinse was mixed with 180 µL BBS buffer and used as stock tears solution. This stock was further diluted by a factor of ten with either water, (for MALDI-TOF analysis) or HBS buffer (for Mass Spectrometric Immuno-Assay (MSIA) analysis).

Plasma. 44.7 µL of human whole blood were collected under sterile conditions from a lancet-punctured finger using a heparinized microcolumn (Drummond Scientific Co., Broomall, Pa.), mixed with 205 µL HBS buffer and centrifuged for 30 seconds (at 7,000×g) to pellet the red blood cells: A 50 µL aliquot of the supernatant was mixed with 200 µL HBS and the resulting solution was used for MSIA; an aliquot was further diluted (10 fold) with ddH$_2$O for MALDI-TOF analysis.

Saliva. Human whole saliva was diluted by a factor of 100 in ddH$_2$O or HBS buffer in preparation for MALDI-TOF or MSIA, respectively.

Urine. Human urine was prepared for MALDI-TOF by a 100-fold dilution with ddH$_2$O; a two-fold dilution with HBS buffer was used for MSIA.

Mass Spectrometric Immunoassay (MSIA)

MSIA was performed on the biological fluids by repeatedly drawing a fluid (~20 times) through an anti-$\beta_2$m-affinity pipette using a hand-held P-200 micropipettor. After the repetitive-flow incubation, the affinity pipette was rinsed with 2 mL of HBS buffer (by drawing the HBS through in 200 µL aliquots and then discarding), followed by a 1 mL rinse with ddH$_2$O (using the same wash and discard approach). At the final discard of the water rinse, it was checked that all residual water was expelled from the affinity pipette. The retained compounds were eluted from the affinity pipette by drawing a 3 µL aliquot of matrix solution (saturated solution of α-cyano-4-hydroxycinnamic acid (ACCA; Aldrich, Milwaukee, Wis.) in 1:2, acetonitrile: ddH$_2$O, 0.2% TFA) into the affinity pipette (enough to cover the microcolumn), upon which the matrix/eluent mix was deposited directly onto a MALDI-TOF target. MALDI-TOF mass spectrometry was performed using a mass spectrometer. Briefly, the instrument uses a two-stage 30 kV (2×1 cm; 15 kV/stage) continuous-extraction source to accelerate ions to the entrance of a 1.4 m flight tube containing an ion guide-wire. Ions generated using a pulsed N$_2$ laser (337 nm) were detected using a hybrid single channel plate/discreet dynode multiplier biased at −3.8 kV. Spectra were recorded using an averaging transient recorder while monitoring individual laser shots using a separate oscilloscope and attenuating laser intensity (in real-time) during acquisition. All spectra were acquired in the positive-ion mode.

Quantification

Internal reference. Equine $\beta_2$m (E$\beta_2$m) was chosen as an internal reference for quantification because of its high degree of similarity to human $\beta_2$m (H$\beta_2$m) (~75% sequence homology), resolvable mass difference from H$\beta_2$m (MW$_{E\beta 2m}$=11,402.9; MW$_{H\beta 2m}$=11,729.7) and because it was easily obtainable. Horse urine was collected fresh (at a local stable) and treated immediately with protease inhibitor cocktail. Low solubility compounds were removed from the urine by overnight refrigeration (at 4° C.) followed by centrifugation for 5 minutes at 5,000×g. The urine was then concentrated 20-fold over a 10-kDa MW cut-off filter, with repetitive HBS and water rinses and with several filter exchanges (4 filters/200 mL urine). Treatment of 200 mL fresh urine resulted in 10 mL of $\beta_2$m-enriched horse urine which served as stock internal reference solution for ~100 analyses.

Working curve. Quantification of H$\beta_2$m was performed. Briefly, standards were prepared by step-wise dilution (i.e., ×0.8, 0.6, 0.4, 0.2 and 0.1, in HBS) of a 1.0 mg/L stock H$\beta_2$m solution to a concentration of 0.1 mg/L; the 0.1 mg/L solution served as stock for an identical step-wise dilution covering the second decade in concentration (0.01-0.1 mg/L). A blank solution containing no H$\beta_2$m was also prepared. The samples for MSIA were prepared by mixing 100 µL of each of the standards with 100 µL of stock horse urine and 200 µL of HBS buffer. MSIA was performed on each sample as described above, resulting in the simultaneous extraction of both E$\beta_2$m and H$\beta_2$m. Ten 65-laser-shots MALDI-TOF spectra were taken from each sample, with each spectrum taken from a different location on the target. Care was taken during data acquisition to maintain the ion signals in the upper 50-80% of the y-axis range and to avoid driving individual laser shots into saturation. Spectra were normalized to the E$\beta_2$m signal through baseline integration, and the integral of H$\beta_2$m was determined. Integrals from the ten spectra taken for each calibration standard were averaged and the standard deviation calculated. A calibration curve was constructed by plotting the average of the normalized integrals for each standard versus the H$\beta_2$m concentration.

Screening. Urine samples were collected from individuals, treated with protease inhibitor cocktail and cooled to 4° C. The urine samples were centrifuged for 5 minutes (at 5000×g) immediately prior to analysis to remove any precipitated material. In preparation for MSIA, 100 µL of each urine sample was mixed with 100 µL of stock horse urine and 200 µL of HBS. This treatment is identical to that used in preparation of the working curve, with the exception of replacing the standard with the human urine sample. MSIA was performed as described in the working curve section.

Affinity pipette Evaluation/Biological fluids Screening.

Figure 2B:
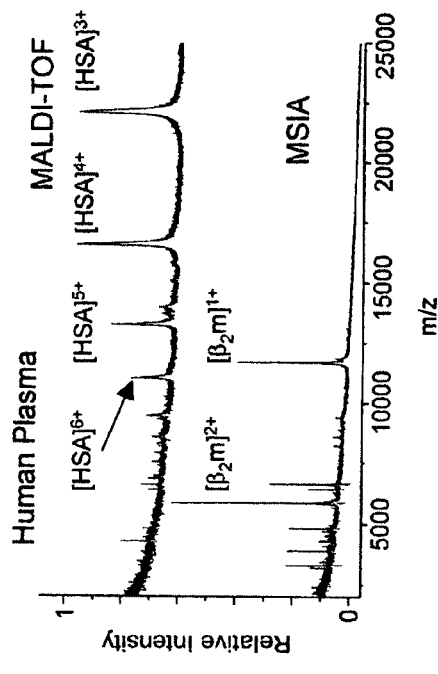
FIG. 2 $\beta_2$-microglobulin MSIA screening of biological fluids. Samples were prepared by dilution of the biological fluid with HBS (H$_2$O for standalone MALDI-TOF) and repetitive flow incubation through the affinity pipette. Affinity pipettes were washed using HBS and water before elution of retained compounds directly onto a mass spectrometer target using ACCA (saturated in 1:2, ACN:H$_2$O; 0.2% TFA). (A) Human tears. (B) Human plasma. (C) Human saliva the saliva required an additional rinse with 0.05% SDS (in water) to reduce non-specific binding. (D) Human urine. In all cases, $\beta_2$m was efficiently retrieved from the biological fluids using the flow-incubate/rinse procedure. The masses determined for the $\beta_2$m (using external calibration) were within ~0.1% of the calculated value (MW$_{calc}$=11,729.7; MW$_{tears}$=11,735; MW$_{plasma}$=11734; MW$_{saliva}$=11,742; MW$_{urine}$=11,735). Illustrating diverse biological fluid screening by MSIA for a directed, rapid, sensitive and accurate analysis.
Figure 2D:
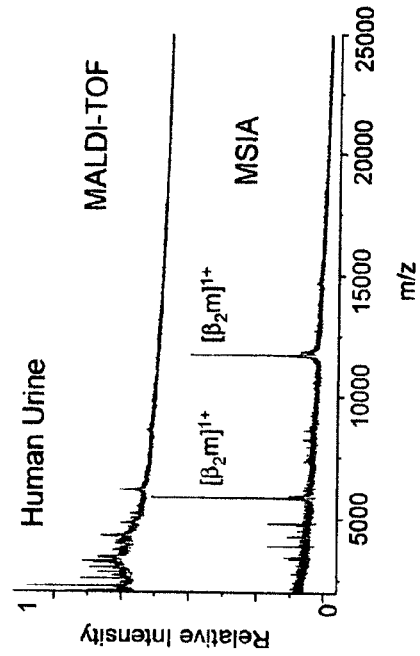
Figure 2A:
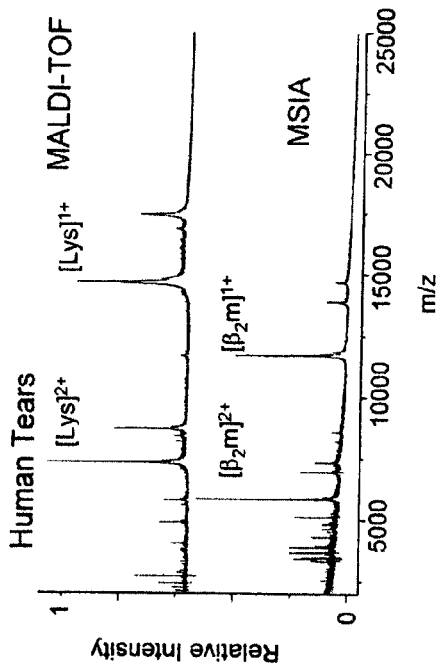
Figure 2C:
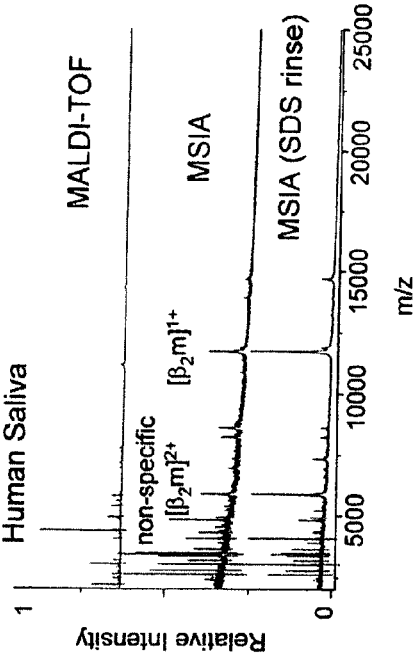

The affinity pipettes were evaluated by screening a number of easily obtainable biological fluids. The intent of the screen was to gauge the degree of non-specific binding encountered from each of the fluids and to briefly investigate alternative rinsing protocols that reduce contributions from non-specific binding. FIG. 2a shows a MALDI-TOF spectrum of diluted human tear and a spectrum showing tear compounds retained during MSIA. High-level proteins present in the tears dominate the MALDI-TOF spectrum: lysozyme (MW$_{calc}$=14,696; MW$_{obs}$=14,691) and tear lipocalin (MW$_{calc}$=17,444; MW$_{obs}$=17,440). Other polypeptide signals are observed in the 2-5 kDa range, as well as a low-intensity signal at m/z=11,727 Da, presumably due to $\beta_2$m. The MSIA spectrum shows signals due to the selectively retained $\beta_2$m (MW$_{calc}$ 11,729; MW$_{obs}$=11,731) and attenuated signals for the lysozyme and other non-specified compounds. FIG. 2b shows MALDI-TOF and MSIA spectra of diluted human plasma. As is commonly observed during direct analysis of serum or plasma, the MALDI-TOF spectrum is dominated by signals originating from albumin. Other lower m/z signals are also present; however, $\beta_2$m signals are not observed. The MSIA spectrum shows strong signals due to the selectively retained $\beta_2$m and few other signals from non-specified compounds. FIG. 2c shows spectra of diluted saliva (MALDI-TOF) and salivary proteins retained during MSIA. The MALDI-TOF spectrum shows a number of signals in the 1-18 kDa range, most prominently in the peptide region; signals corresponding to $\beta_2$m are not observed. The MSIA spectrum, obtained after using the normal rinse protocols, shows signals due to the selectively retained $\beta_2$m and an abundance of non-specified compounds in the low molecular mass range. A second MSIA analysis was performed in which an additional rinse with 0.05% sodium dodecylsulfate (SDS) was included between the BBS and the ddH$_2$O rinses (FIG. 2c). The SDS rinse, although not completely eliminating the low mass signals, did significantly reduce their contribution to the mass spectrum without a proportional reduction of the $\beta_2$m signal. FIG. 2d shows spectra resulting from the analysis of human urine. The MALDI-TOF spectrum shows a number of signals in the peptide region and an absence of signal for $\beta_2$m. The MSIA spectrum is dominated by signals from the $\beta_2$m, with few additional signals from non-specified compounds.

The porous glass molecular traps used in the affinity pipettes performed well in the screening of the biological fluids. Intermediate CMD amplification of the amine functionalized porous glass molecular traps provided a largely hydrophilic surface with multiple attachment points (carboxylic acid groups) for coupling of the antibody. As a result, the antibody load of each affinity pipette is more than sufficient to capture low levels of $\beta_2$m without saturation of the antibody. Also, the hydrophilic surface can be washed free of most non-specifically bound compounds by rinsing with aqueous ionic buffers. With the exception of the saliva sample, MSIA exhibited reasonably clean mass spectra showing predominantly signals derived from $\beta_2$m. The SDS wash of the saliva screen, although improving spectral quality, did not completely eliminate all of the non-specified compounds. Upon closer investigation it is found that those compounds (identified by mass as lysozyme, $\alpha$-defensins and histatins) have pIs of ~10, suggesting retention via charge interactions (with free-carboxyl groups) that are not broken by the moderate pH (7.8) and salt (150 mM NaCl) content of the HBS buffer. Thus, other rinsing combinations (e.g., high-salt or different detergents) will need to be investigated if the salivary screen is deemed to be of biological significance. It is worth noting, however, that the presence of the non-specified compounds (in any of the samples) did not interfere with the unambiguous determination $\beta_2$m, which was identified by virtue of direct detection at its characteristic molecular mass.

Quantification

Protein quantification using MALDI-TOF requires use of internal standards to compensate for varying laser intensities and spot-to-spot differences in sample composition that give rise to fluctuations in analyte ion signal. Although proteins with characteristics unlike those of the analyte may be used as internal standards (as has been shown during protein quantification directly from mixtures or during MALDI-TOF quantification of affinity-retrieved species by addition of an internal reference standard to peptides eluted from beaded affinity media), internal reference standards that behave similarly to the analyte during laser desorption/ionization are generally preferred. This prerequisite is met during MSIA by choosing internal references that share sequence homology with the target protein: enzymatic/chemically-modified versions of the targeted protein, truncated/extended recombinant forms of the target proteins, the (same) target protein recombinantly expressed in isotopically-enriched media (e.g., $^{15}$N or $^{18}$O) or the same protein from a different biological species. Given that the receptor is able to capture both the target protein and the internal reference, MSIA can be designed around a single receptor system. Alternatively, a two-receptor system can be considered where one receptor is used to retrieve the target protein and a separate receptor is used to retrieve the internal reference.

Figure 3B:
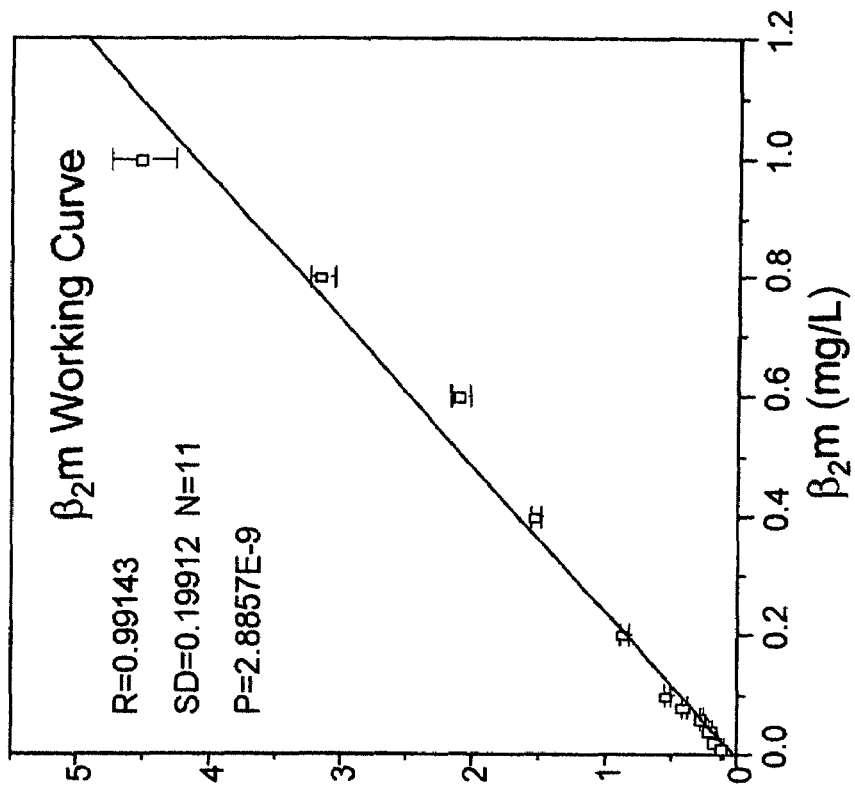
FIG. 3b Working curve generated using the data represented in FIG. 3a. The two-decade range was spanned with good linearity ($R^2$=0.983) and low standard error (~5%). Error bars reflect the standard deviation often repetitive 65-laser shots spectra taken from each sample. These figures illustrate quantitative MSIA performed via $\beta_2$m-affinity pipettes.
Figure 3A:
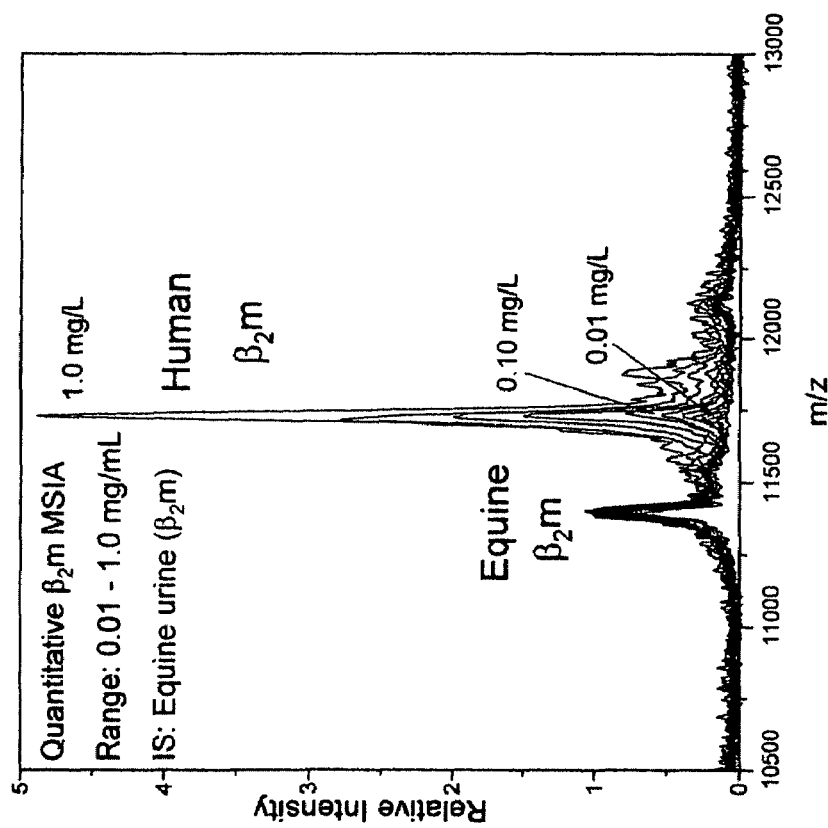
FIG. 3a Quantitative $\beta$2m-MSIA—working curve. Representative spectra of data used to generate the working curve. Human $\beta_2$m concentrations of 0.01-1.0 mg/L were investigated. Equine $\beta_2$m (MW=11,396.6) was used as an internal standard.

The internal reference chosen herein was equine $\beta_2$m (E$\beta_2$m), which shares ~75% homology with its human counterpart and is ~300 Da lower in mass than H$\beta_2$m (thus, both species share similar characteristics and are easily resolved in the mass spectra). Even though no data could be found on the relative dissociation constants between the polyclonal anti-$\beta_2$m IgG and H$\beta_2$m or E$\beta_2$m, preliminary studies showed that the antibody exhibited cross-reactivity sufficient to retain both species. FIG. 3a shows spectra representing MSIA analyses of H$\beta_2$m standards in a concentration range of 0.01-1.0 mg/L. Each spectrum, normalized to the E$\beta_2$m signal, is one often 65-laser shots spectra taken for each calibration point. Plotting the average of the 10 normalized H$\beta_2$m integrals for each standard versus the H$\beta_2$m concentration results in the working curve shown in FIG. 3b. Linear regression fitting of the data yields $I_{H\beta2m}/I_{E\beta2m}$=4.09 [H$\beta_2$m in mg/L]+ 0.021 ($R^2$=0.983), with a working limit of detection at a S/N>3 of 0.0025 mg/L (210 pM) and a limit of quantification of 0.01 mg/L (850 μM). The standard error of all points of the working curve is ~5%.

Quantitative Determination of $\beta_2$m in Urine Samples

Figure 4:
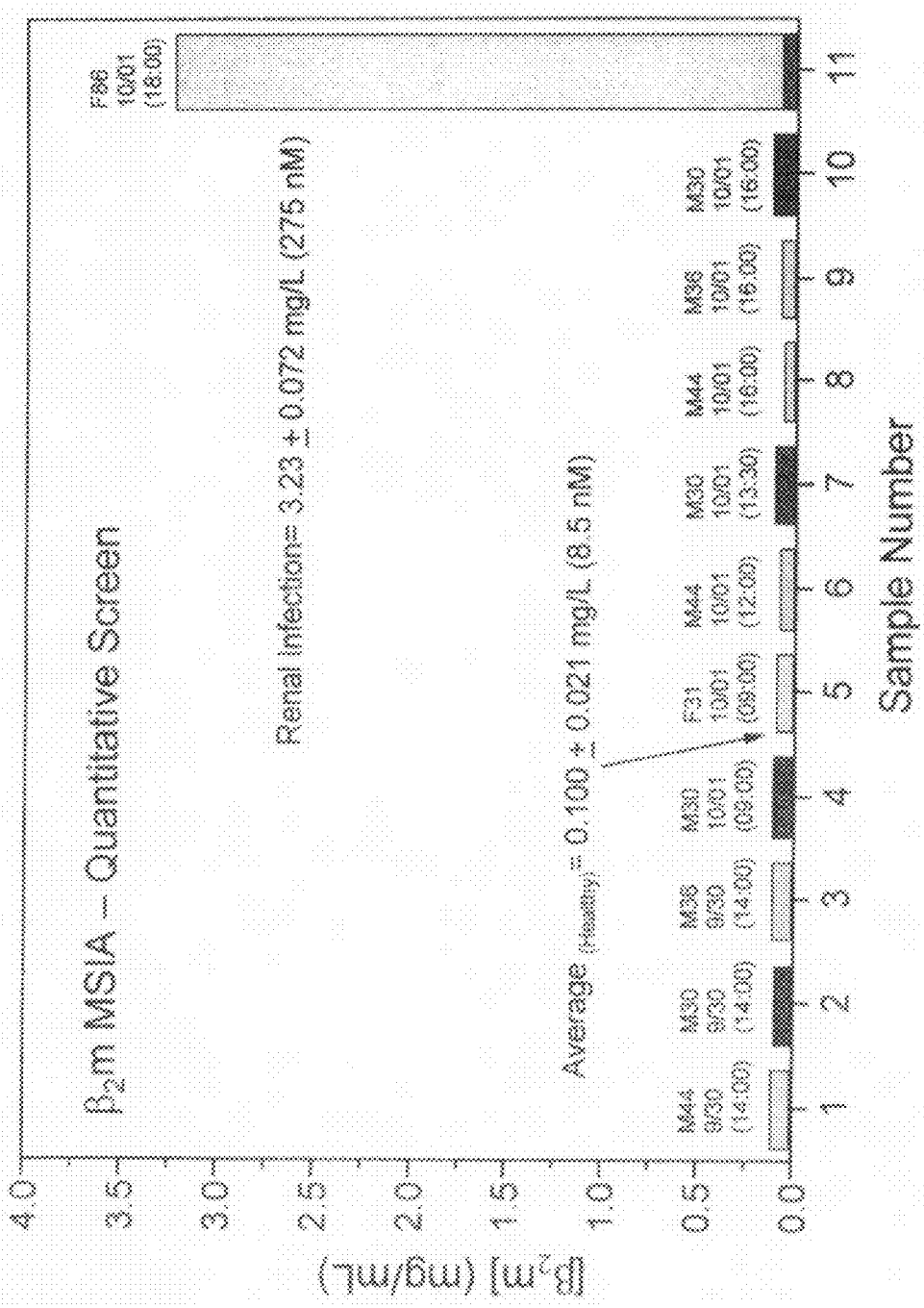
FIG. 4 Quantitative $\beta$2m-MSIA—screening. Human urine samples from five individuals were screened over a period of two days. The average value determined for healthy individuals (10-samples; 4-individuals (3 male; 1 female) ages 30-44 years) was 0.100±0.021 mg/L. The level determined for an 86-year old female with a recent urinary tract infection indicated a significant increase in $\beta_2$m concentration (3.23±0.072 mg/L).

Ten samples were collected from four individuals: female (31 years, pregnant; 1-sample (F31)), male (30 years; 4-samples over two days (M30)), male (36 years; 2-samples over two days (M36)) and male (44 years; 3-samples over two days (M44)). All of the individuals were in a state of good health when the samples were collected. Results from MSIA of the ten urine samples are shown in FIG. 4. The bars depict the $\beta_2$m concentration determined for each sample, while the inset spectra above each bar show the respective H$\beta_2$m signals normalized to E$\beta_2$m. The data for the ten samples show remarkable consistency, with an average $\beta_2$m concentration of 0.100±0.021 mg/L (high=0.127 mg/L; low=0.058 mg/L). An additional analysis was performed on a urine sample obtained from an 86-year old female (F86) who had recently suffered a renal infection. Because of the significantly higher level of $\beta_2$m found in this sample (see inset spectrum) it was necessary to quantitatively dilute the urine by a factor of ten in order to keep the $\beta_2$m signal inside the dynamic range of the working curve and accurately establish the $\beta_2$m concentration in F86 (at 3.23±0.02 mg/L).

Post Translational Modifications

Figure 5:
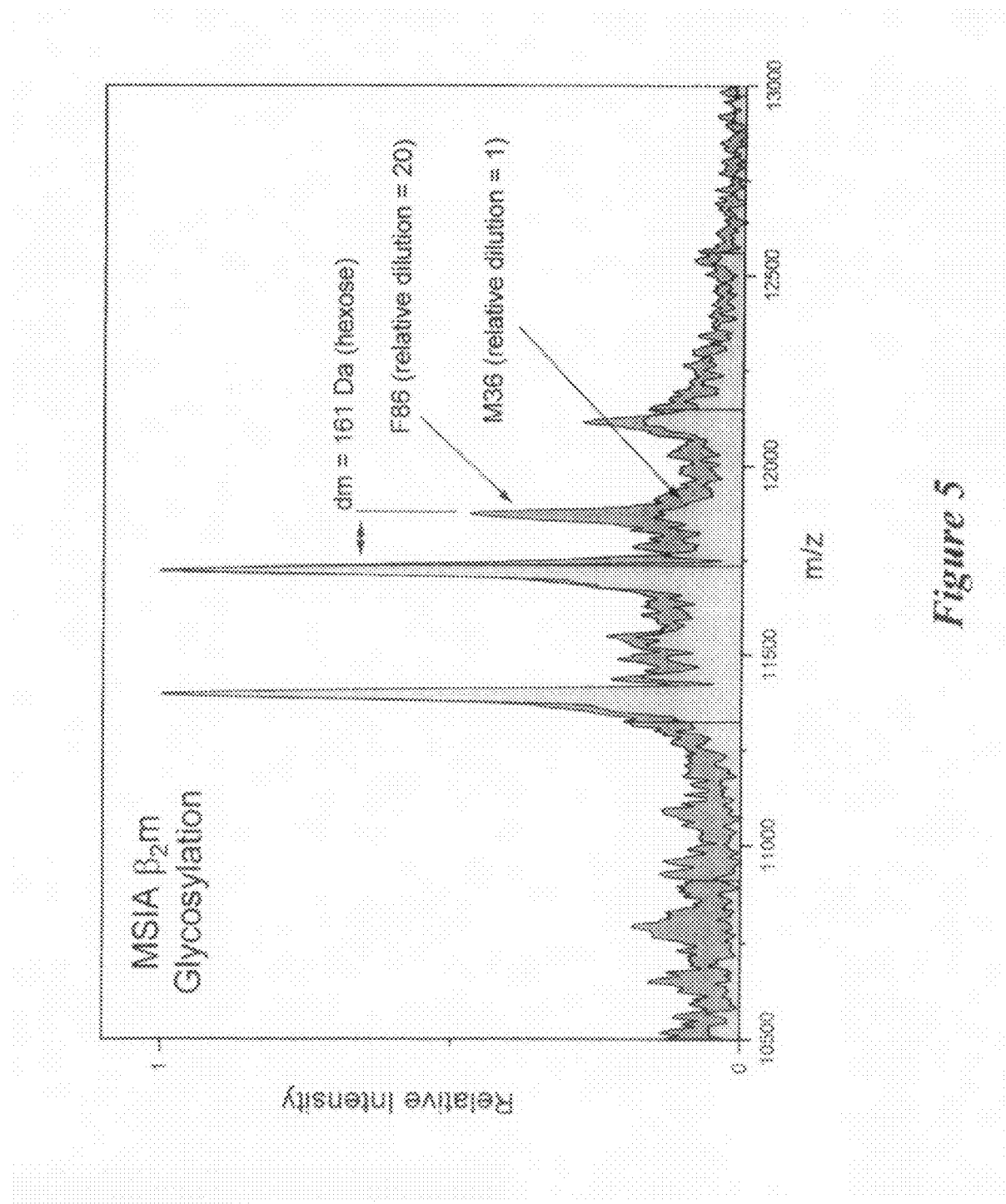
FIG. 5 MSIA showing elevated level of glycosylated $\beta_2$m in a 86-year old female (dark gray). During MSIA, a second signal is observed at $\Delta$m=+161 Da, indicating the presence of glycosylated $\beta_2$m. MSIA is able to adequately resolve the two $\beta_2$m forms, resulting in a more accurate quantification of the nascent $\beta_2$m and possible quantification of the glycoprotein. Such differentiation is important considering that the two $\beta_2$m forms originate from (or are markers for) different ailments. MSIA of a healthy individual, showing little glycosylation, is given for comparison (light gray).

The mass-selective detection of MSIA makes possible the discovery and quantification of variants of $\beta_2$m that may be present in urine. During quantitative screening of the urine samples, a second, higher molecular mass species ($\Delta$m=+161 Da) was co-extracted with the $\beta_2$m. The species is presumably a glycosylated (one hexose) form of $\beta_2$m, and is observed most prominently in F86. FIG. 5 shows an overlay of two MSIA spectra taken from the urine of F86 (diluted×20) and M36 (no dilution; given for comparison). The level of glycosylated $\beta_2$m is much greater in F86 than in M36. The specific cause of the elevated level of the glyco-$\beta_2$m is at present uncertain.

Previous work has reported the quantification of glycosylated H$\beta_2$m by direct MALDI-TOF analysis of serum into which glycosylated H$\beta_2$m was doped at reasonably high concentrations. Due to poor mass spectral resolution and interferences from the serum, a curve-fitting routine was used to deconvolute signals from multiple H$\beta_2$m glycoforms, the integrals of which were then normalized to wild type $\beta_2$m for use in constructing a working curve of reasonable linearity ($R^2$=0.88). Although the data presented here is significantly better and clearly able to support rigorous quantification without aid of fitting routines, it is uncertain whether the working curve constructed for the unmodified $\beta_2$m can be used directly for the rigorous quantification of the glycosylated $\beta_2$m. Such correlation requires that the affinity constants for, and the desorption/ionization efficiency of, both $\beta_2m$ forms are equal. Regarding the affinity constants, the affinity-purified polyclonal antibody used herein clearly shows broad cross-reactivity (as demonstrated by the co-extraction of $H\beta_2m$ and $E\beta_2m$) so it is highly probable that both $H\beta_2m$. forms are extracted with similar efficiencies. Similarly, the addition of a single carbohydrate moiety should not severely attenuate the relative desorption/ionization efficiency. As a result, the concentration of the glycosylated $\beta_2m$ form might be estimated using the $\beta_2m$-working curve at 0.072 mg/L— roughly the same concentration as wild type $\beta_2m$ in the urine samples from the healthy individuals.

Regardless of whether both wild type and glycosylated $\beta_2m$ can be quantified using a single working curve, it is important to note that the concentration of the wild type $\beta_2m$ determined during MSIA does accurately reflect the concentration of only the wild type $\beta_2m$ and not the combination of both of the species. Thus, MSIA holds a particular advantage over other techniques that are unable to differentiate between similar forms of a target analyte. In that elevated $\beta_2m$ levels are used as a general indicator of immune system activity, while $\beta_2m$-glycosylation has been associated with more specific ailments (e.g. advanced glycosylated end-products associated with dialysis related amyloidosis), MSIA is able to deconvolute these independent contributing factors and yield results that more accurately connect a specific biomarker with a specific ailment.

The manufacturing process used in this report yielded affinity pipettes with an estimated binding capacity of 10-100 pmol, while having a dead volume of approximately 1.5 µL. This binding/elution ratio was found to adequately match the $\beta_2m$ concentrations found in the biological fluids. Moreover, the efficient capture of $\beta_2m$ using the affinity pipettes kept the sampling volume low (less than 100 µL of biological fluid). In addition, the affinity pipette chemistries employed herein exhibited little non-specific binding for three of the four biological fluids, and even in the fourth (saliva) did not introduce analytical interferences into the analysis.

The quantitative capabilities of MSIA are clearly demonstrated in the present invention. The $\beta_2m$ concentration range investigated herein (0.010-1.0 mg/L) is adequate to cover the $\beta_2m$ levels in all fluids. Good linearity is observed over the two decade ranges ($R^2$=0.983) with an overall error of ~5%. Important to accurate quantification is the choice of an appropriate reference standard, which in this example was fulfilled by use of horse urine enriched in $\beta_2m$. However, even though the horse urine is viewed as an ideal background media (because it more closely mimics the true analytical media than buffers), it will need to be replaced in future analyses with purified $E\beta_2m$ in order to ensure consistency when analyzing a large number of samples over long periods of time.

Although the screening study presented here was not extensive enough to be considered a clinical study, it does demonstrate the utility of MSIA in accurately identifying and quantifying $\beta_2m$ directly in biological samples, such as urine samples. The four baseline individuals contributing urine to the project were considered healthy, not suffering from any known genetic afflictions linked to $\beta_2m$ or having suffered from any ailments in the month immediately preceding the analyses. Qualitative evaluation of the $\beta_2m$ retained from the samples revealed single signals for $\beta_2m$ with molecular mass corresponding to the wild-type sequence of the protein (within 0.02% experimental error; spectra internally calibrated by using the $E\beta_2m$ signals; see FIG. 4). Quantitative analysis within the group showed remarkably constant $\beta_2m$ levels that are consistent with those found in control groups during other studies. By contrast, the urine sample obtained from an older individual of poor health showed a marked increase in urinary $\beta_2m$ level (~30-times greater). It should be noted that this estimate was made without interference from a higher-mass variant of $\beta_2m$, which was readily detectable in the mass spectra (see FIG. 5). The most reasonable explanation for the observation of two mass-shifted (yet related) signals in the mass spectrum is the presence of: 1) the wild-type protein, and 2) a variant existing due to either a genetic polymorphism or a posttranslational modification. In this particular case, the variant is most easily identified by the mass shift of +161 Da as a glycosylated form of $\beta_2m$; variants due to genetic polymorphisms are essentially ruled out because the mass shift is greater than that resulting from any single nucleotide polymorphism (i.e., [TGG]-[GGG]; resulting in Trp-Gly; dm=129.15 Da). However, had variants possessing a significant mass shift (>15 Da) as a result of a genetic polymorphism been present in the sample, they would have been as readily recognized as the glycosylated $\beta_2m$.

Lastly, in that MSIA analyses are fairly rapid and relatively easy to perform, the approach lends itself particularly well to the rapid development of analytical methods and the analysis of large numbers of samples. The rapid rate of analysis opens the possibility of real-time method development in which changes in incubation and rinse protocols can be readily implemented when the results from a just completed trial are analyzed. Once developed and optimized, these methods could be readily applied to screening of biological fluids. Herein the samples were analyzed at a rate of ~3/hour, which allowed for several analyses to be performed on a given individual within a single day (as shown in FIG. 4, M30). This rate of analysis was essentially limited by instrumentation that is not designed to accommodate multiple samples—each analysis herein (preparation-through-analysis) was performed individually. However, it is feasible to increase this rate of analysis to hundreds-per-day by use of parallel pipetting stations and mass spectrometers that accept multiple samples on an arrayed format. In this manner, pipetting stations addressing 96-well format titer plates will now be described to simultaneously prepare, modify, incubate, capture and rinse the multiple samples using multiplexed affinity pipettes. The samples are then eluted onto a mass spectrometer target array of the same format.

Robotic Integration

Figure 7A:
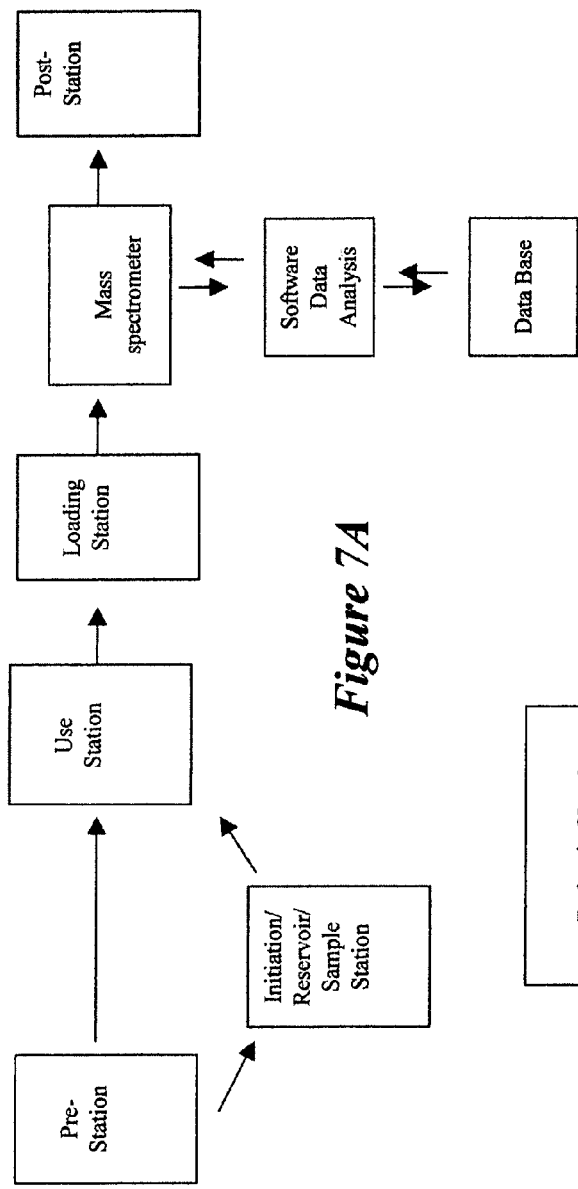
FIG. 7a is a schematic illustration describing the integrated system for high-throughput analysis of biomolecules from biological media.

The mass assay system, FIG. 7a, is a system for high throughput nascent biological fluid analyte extraction by affinity microcolumns within a conduit system comprising one or more functional pre-, use, analysis, and post-stations. The pre-stations initiate sample information, organize, prepare and formulate components, sample arrays and targets for primary and analysis workstation use. Sample identification, performed on incoming biological fluids, which ascertains initial sample parameters, such as bio-sample type (blood, urine, cell culture media, etc.), patient history, disease state, chemical parameter profile (pH, turbidity, etc.), and the like, results in a sample classification database for integration with final output analysis data promoting congruent and feedback databases. Pre-station high performance fluid manipulation, with accompanying labeling and tracking, allows for distribution of identified biological fluid from sample source into compartmentalized individual sampling array, labeled (e.g., bar-code/laser reader) for tracking, with further inline manipulation, such as appropriate dilution or modification (pH, surfactant addition, etc.). Another function of the pre-station is formulation and loading of the array components. Here, component arrays, including, but not limited to, solid components (plastics, glasses, metals and the like), fluid reagents, targets and the like, are formed and/or distributed into appropriate arrays and loaded into the primary workstation. From the prestation, the array of molecular traps are accessed by an initiation/reservoir/sample station, the primary station, or relocated to a use station for sample processing.

Example processes performed in the prestation include, but are not limited to, assembly of porous molecular traps into affinity pipettes, array labeling, sample preparation, sample modification. These processes are carried out using solid sample array(s) (plastic microtiter plates, etc.), array labels, chemical/modifying reagent (e.g. storage reagents, activation reagents, buffers, surfactants, reducing reagents, etc.), affinity reagents and ligands (biological mimics, antibody(s), antigen(s), etc.), rinse fluids (buffers, ultra pure water, etc.), desorption fluids (MALDI matrix, acids, bases, surfactants, etc.) and analysis target(s).

The pre station combines ligand and analyte in separate microcolumn activation, sample retrieval/separation and sample transfer/elution functions. Preferably, multiple samples are loaded into the pre station and spatially arranged in an array commensurate with the array of molecular traps with one sample for each molecular trap in the array of molecular traps.

From the pre station, the array of samples is automatically relocated to a use station. The use station is where the sample, and specific analytes contained therein are processed. In one embodiment, one end of the array of molecular traps is lowered into the sample and the same sample is drawn into each molecular trap. Since each molecular trap has affinity receptors located on surfaces of the molecular trap, drawing the sample into the molecular trap contacts any specific analyte sought after with the affinity receptors. In the array, each molecular trap may have different affinity receptors from that of other molecular traps in the array, thereby enabling the targeting of different specific analytes from the same or different media. Sample material may be drawn into the molecular trap singly or multiple times. After sufficient specific analyte has been captured by the molecular traps in the array, residual, or non-captured, media are washed away with at least one rinse. (However, other embodiments may not require a rinse step.) After non-targeted compounds have been washed away, captured specific analyte are eluted from the molecular traps by contacting them with a solution selected to interrupt the affinity interaction. The eluted specific analytes are then either prepared directly for mass spectrometry or for further processing, e.g., enzymatical/chemical modification, followed by subsequent preparation for mass spectrometry. The pre stations may comprise multiple positions for chemical modification, molecular trap functionalization, biological fluids analysis and/or transfer. Finally, the eluted specific analytes are relocated to a target array by stamping them onto the target array.

Figure 7B:
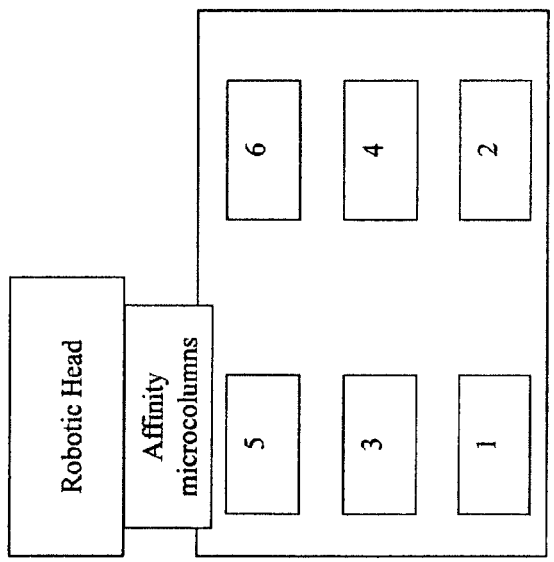

With reference to FIG. 7b, a preferred embodiment of the use station further comprises a microcolumn manifold to which the array of molecular traps are attached. The microcolumn manifold attaches to a robotic head that then physically moves the array of molecular traps between each processing station. This physical movement of the microcolumn manifold may be in a rectangular (xy) or circular (carousel) manner. Alternatively, the microcolumn manifold in the use station may be stationary and the processing stations relocated under the array of molecular traps. Like the physical movement of the microcolumn array described above, the physical movement of the processing stations may be in a rectangular (xy) or circular (carousel) manner. A further embodiment contemplates the physical movement of both the microcolumn manifold and the processing stations together.

In a preferred embodiment, the target array is automatically relocated to a storing/loading station that is capable of containing at least one target array. From the storing/loading station, the target array is transferred into an automated mass spectrometer capable of multi-sample input and automatic processing/data analysis using an interactive database.

Automated mass spectrometry is performed with either the specific analyte or modified fragments detected with high precision. Software capable of recognizing differences between samples, or from a standard, is used to aid in the analysis of large numbers of samples and generate proprietary databases from which to establish novel information systems i.e., structure function systems, clinical systems, diagnostic systems and biochemical systems. Biochemical systems generally refer to a chemical interaction that involves molecules of the type generally found within living organisms, including the full range of catabolic and anabolic reactions which occur in living systems such as enzymatic, binding, signaling and other reactions. Other, biochemical systems, includes model systems that are mimetic of a particular biochemical interaction. Examples demonstrated within the context of this present invention or of interest in practicing the present invention include, e.g., receptor-ligand interactions, protein-protein interactions, enzyme-substrate interactions, cellular signaling pathways, transport reactions, genotyping and phenotyping.

After analysis by mass spectrometry, the target array may be transferred to a post-station for sample processing or additional analysis subsequent to the mass spectrometric analysis.

Accordingly, in one aspect, the present invention will be useful in screening for ligands or compounds that affect an interaction between a receptor molecule and its ligand.

In-Robot Functionality

Example 19

In-Robot Amine Activation/Derivatization of Functionalized Porous Molecular Traps Another approach involves robotic integration of the previously mentioned formats during which such protocols as glutaraldehye activation and ligand coupling, are used in a concerted in-robot activation/derivatization. Here, amine functionalized porous glass molecular traps are dry loaded/seated (either manually or machine assisted) into warm p-200 wide bore pipette affinity pipettes (Robbins Corp.) and loaded into a plastic 96 rack. This rack is integrated onto station one of a six-staged robot, loaded with microtiter plates containing various coupling and rinsing solutions, that is linked to a personal computer and software controlled. Glutaraldehye coupling to amine microcolumns occurs via a first 96 well microtiter plate containing 110 µL per well of 25% glutaraldehyde solution in 0.10 M sodium phosphate buffer, pH 7.8, stationed at position two, using one-hundred aspiration repetitions. This initial coupling step requires extensive HBS buffer rinses (110 µL/well) attained at station three (containing a second 96 well microtiter plate, fifty aspiration repetitions), resulting in a rapid in-robot mediated activation coupling (reaction time 10-20 minutes). After a final water rinse at station four (~fifty aspiration repetitions), the activated aldehyde groups on the glutaraldehye matrix are incubated with the protein antibody of interest at station five (0.1-1 mg/mL, 55 µL/well, 200 aspirations). Uncoupled (excess) antibody is removed by extensive rinsing at station six with HBS buffer (10 mM HEPES pH 7.4, 0.15 M NaCl, 0.005% Surfactant P20, fifty aspiration repetitions).

Example 20

In-Robot Amine Activation, Amplification, Reactivation and Derivatization of Amine Microcolumns An extension of the approach demonstrated above is robotic integration of glutaraldehye activation with subsequent in-robot amplification with recurring activation prior to ligand coupling, as a concerted in-robot activation/amplification/derivatization. In this example, aldehyde functionalized porous glass molecular traps (aldehyde microcolumns) are prepared and loaded into positioned one. Then the activated aldehyde groups on the glutaraldehye microcolumns are incubated with polylysine (30-300 kDa) loaded at position two (110 μL, 1 mg/mL in HBS) of the robot stage, resulting in formation of a polymeric scaffold from which to conduct another round of glutaraldehyde mediated activation and antibody conjugation to the amplified micro-top surface.

This initial coupling step is followed by extensive rinses at station three, fifty aspiration repetitions of HBS buffer, resulting in a rapid in-robot mediated activation coupling (reaction time half an hour). After a final water rinse at station four (~fifty aspiration repetitions), the activated aldehyde groups on the glutaraldehye matrix are incubated with the protein antibody of interest at station five (0.1-1 mg/mL, 55 μL/well, 200 aspiration repetitions) after which the MASSAY microcolumns become affinity pipettes. Uncoupled (excess) antibody is removed by extensive rinsing at station six with HBS buffer (10 mM HEPES pH 7.4, 0.15 M NaCl, 0.005% Surfactant P20).

Example 21

MALDI-TOF Chemically Masked Target Preparation for Microcolumn Elution

Arrayed targets present hydrophilic targets that function to localize analyte samples delivered from microcolumns under eluting conditions. These elution conditions vary depending upon the analysis intent, ranging from the general use of MALDI-TOF matrix (ca., alpha cyano-4-hydroxy cinnamic acid in 1:2 ratio of acetonitrile:0.2% TFA in water), dilute acids, dilute bases, chaotropic agents and the like.

In the present example, the target surface consists of a contrast array where a hydrophillic target functions in concert with a hydrophobic background in a chemical mask prepared for a directed analysis, depending upon the type of biomedia used in the assay of interest. Regardless of the intent, the first requirement is cleaning of the surface in a series of rinses and incubations. Initially the target surface is cleaned with detergent, water rinsed, methanol rinsed, and then incubated with 10-15% hydrogen peroxide solution in water at room temperature (or elevated temperatures) for thirty minutes to one hour, After which the cleaned surface is rinsed in water, methanol, nitrogen dried and the target areas derivatized with the alkyl mercaptan of interest. For a cation exchange surface 11-mercaptoundecanoic or 3-mercapto-1-propanesulfonic acid is used as a saturated solution prepared in an organic solvent (ca., isopropanol). The surface is either coated with a saturated solution of octadecyl mercaptan immediately or rinsed with isopropanol followed by methanol and subsequently coated with a saturated solution of octadecyl mercaptan. A chemically contrasted, or masked, surface results for microcolumn analyte localization and sample analysis by mass spectrometry. These cation exchange surfaces are designed for working in a general biological media and are particularly useful when assaying out of urine. Alternatively, masked targets are generated with positively charged groups for use as anion exchangers.

Example 22

Integrated High Throughput System MALDI-TOF Analysis of Biological Samples

Figure 8:
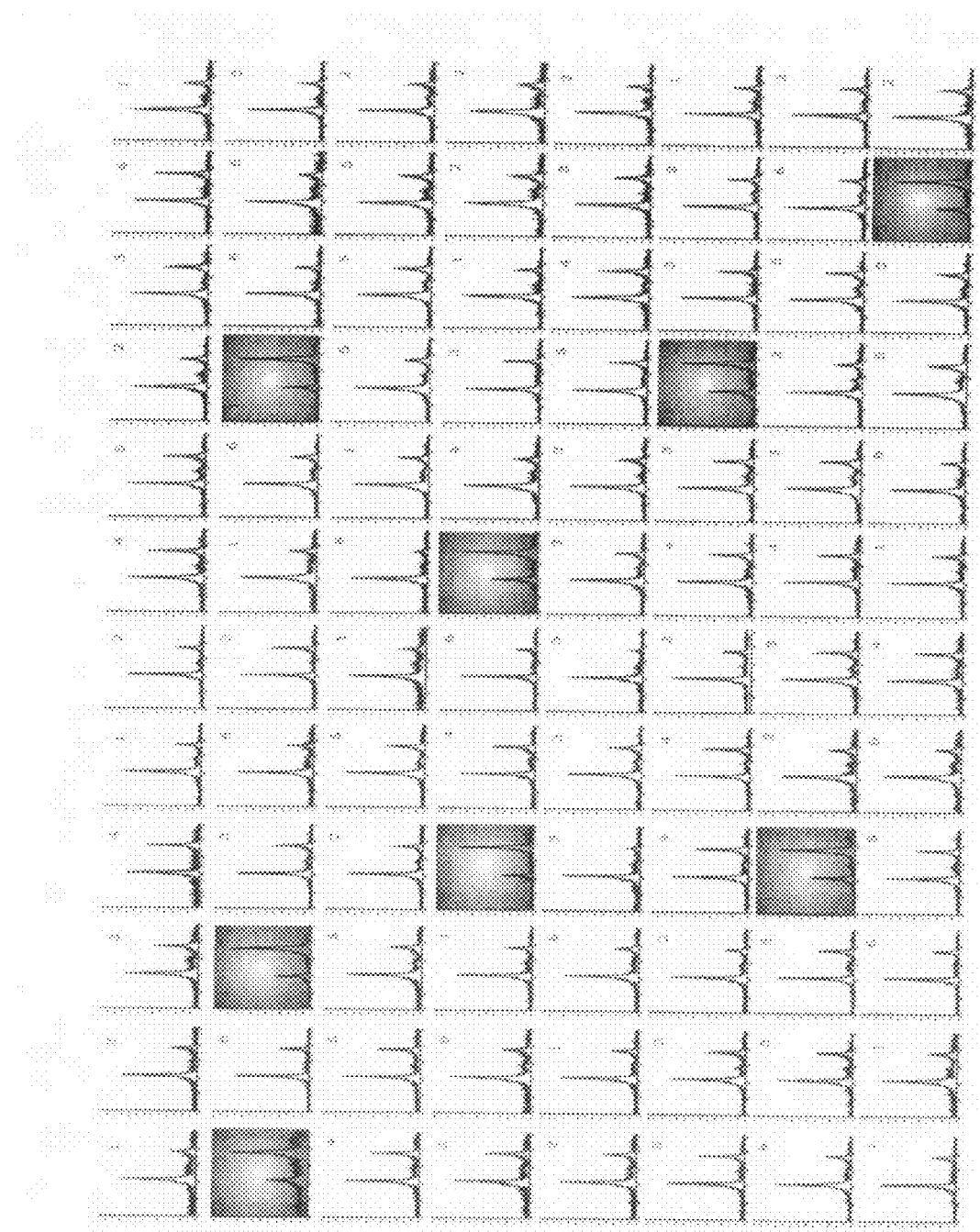
FIG. 8 is an illustration of a high-throughput semi-quantitative analysis of $\beta_2$m MSIA. $\beta_2$m from human plasma samples using the integrated system and methods described in the present invention.

Integrated system parallel processing and analysis of biologically relevant biomolecules out of nascent biological fluids is illustrated in this example demonstrating the capabilities of the high-throughput system. Demonstrated in FIG. 8 is the high-throughput semi-quantitative analysis of beta-2-microglobulin ($\beta_2$m) from human plasma samples performed using the integrated system and methods of the present invention. Aliquots of diluted (5 fold) human plasma samples collected from six individuals were prepared for parallel screening on a 96-well sample plate. Each well received a 15 μL plasma aliquot (the samples from the six individuals were randomized on the 96-well plate), 7.5 μL of equine plasma (undiluted, containing equine $\beta_2$m, $MW_{eq.\beta 2m}$=11,396.6, $MW_{hum.\beta 2m}$=11,729.2) and 128 μL of HBS (0.01 HEPES, pH 7.4, 0.15 M NaCl, 0.005% (v/v) polysorbate 20, 3 mM EDTA) buffer. Eight of the 96 samples were chosen at random and 0.5 μL of $10^{-2}$ mg/mL solution of $\beta_2$m was added to four of them and 1 μL of the same $\beta_2$m solution to the other four wells. Parallel sample processing entailed simultaneous incubation/capture of the 96 samples on 96 anti-$\beta_2$m derivatized microcolumns. The polyclonal anti-$\beta_2$m microcolumns were made via carboxymethyl dextran (CMD)-EDC mediated coupling of the antibody to amino-coated/modified microcolumns. Captured proteins were eluted from the microcolumns with a small volume of MALDI matrix (saturated aqueous solution of α-cyano-4-hydroxycinnamic acid (ACCA), in 33% (v/v) acetonitrile, 0.2% (v/v) trifluoroacetic acid) and stamped onto a MALDI target array surface comprised of self-assembled monolayers (SAM) chemically masked to make hydrophilic/hydrophobic contrast target arrays. Each sample spot on the target array was analyzed using mass spectrometry and the relative $\beta_2$m abundance determined by an automated MALDI-TOF mass spectrometric analysis software routine. The mass spectra resulting from the high-throughput analysis of the 96 samples are shown in FIG. 8. Spectra taken from the samples that had the $\beta_2$m standard solution added are shaded.

Figure 9:
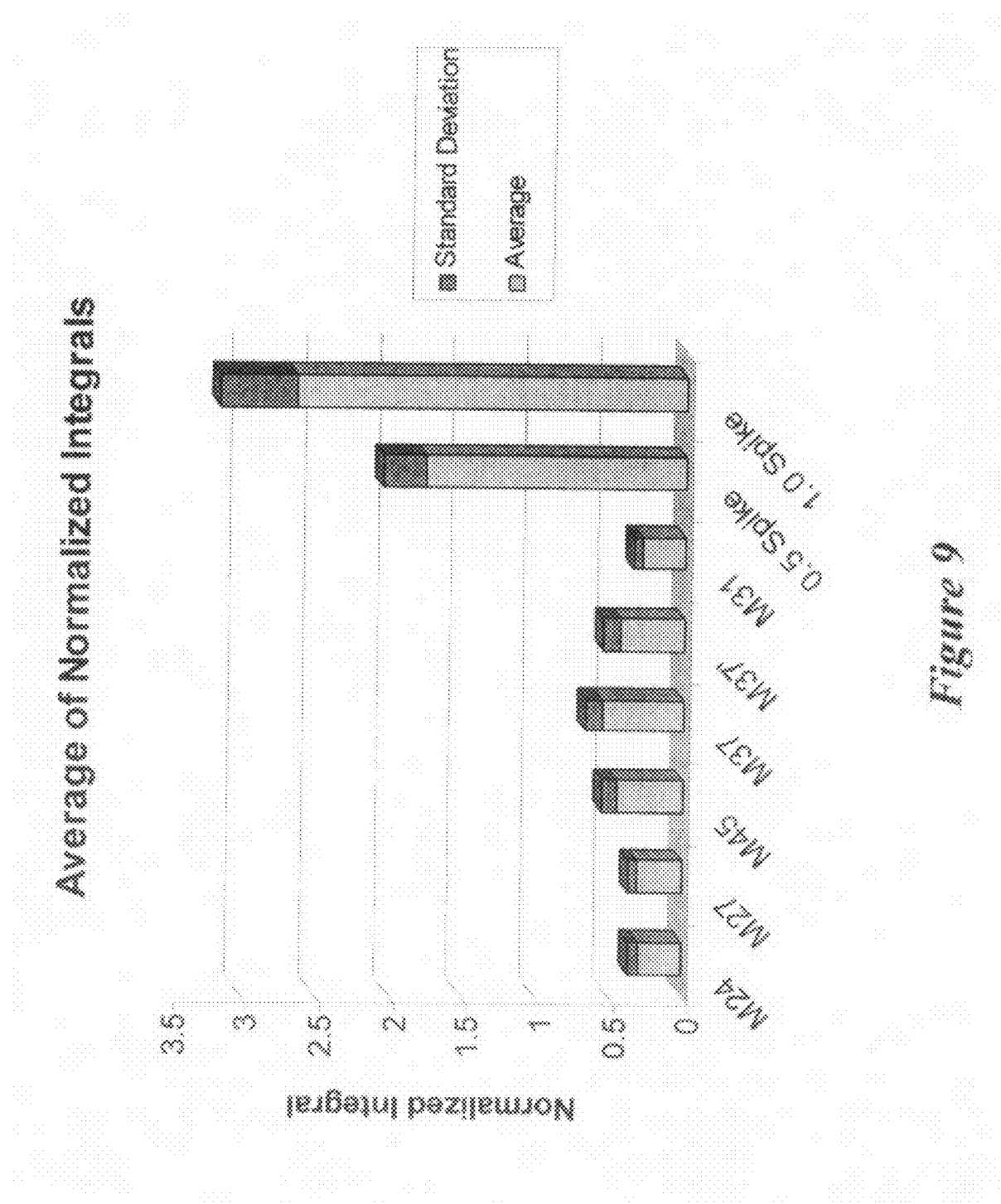
FIG. 9 shows bar graph analysis of the data shown in FIG. 8. Each spectrum shown in FIG. 8 was normalized to the equine $\beta_2$m signal through baseline integration, and the normalized integral for the human $\beta_2$m signal determined. All $\beta_2$m integrals from spectra obtained from sample from the same individual were averaged and the standard deviation calculated. In the same way, the integrals for the samples spiked with 0.5 and 1.0 µL solution of $10^{-2}$ mg/mL $\beta_2$m were calculated and averaged. Plotted in this figure are the average values of the normalized human $\beta_2$m integrals for the samples from the six individuals and the spiked samples. The bar graph clearly establishes increased $\beta_2$m levels in the spiked samples, illustrating the value of the high-throughput semi-quantitative analysis performed with the system and methods described in this invention in establishing increased $\beta_2$m levels in human blood that are associated with various disease states.

FIG. 9 bar graph visualization performs interpretation of the high-throughput system generated semi-quantitative data shown in FIG. 8. Each spectrum shown in FIG. 8 was normalized to the equine $\beta_2$m signal through baseline integration, and the normalized integral for the human $\beta_2$m signal determined. All $\beta_2$m integrals from spectra obtained from samples from the same individual were averaged and the standard deviation calculated. In the same way, the integrals for the samples spiked with 0.5 and 1.0 μL solution of $10^{-2}$ mg/mL $\beta_2$m were calculated and averaged. Plotted in this figure are the average values of the normalized human $\beta_2$m integrals for the samples from the six individuals and the spiked samples. The bar graph clearly establishes increased $\beta_2$m levels in the spiked samples, illustrating the value of the high-throughput semi-quantitative analysis performed with the system and methods described in this invention in establishing increased $\beta_2$m levels in human blood that are associated with various disease states.

Figure 10:
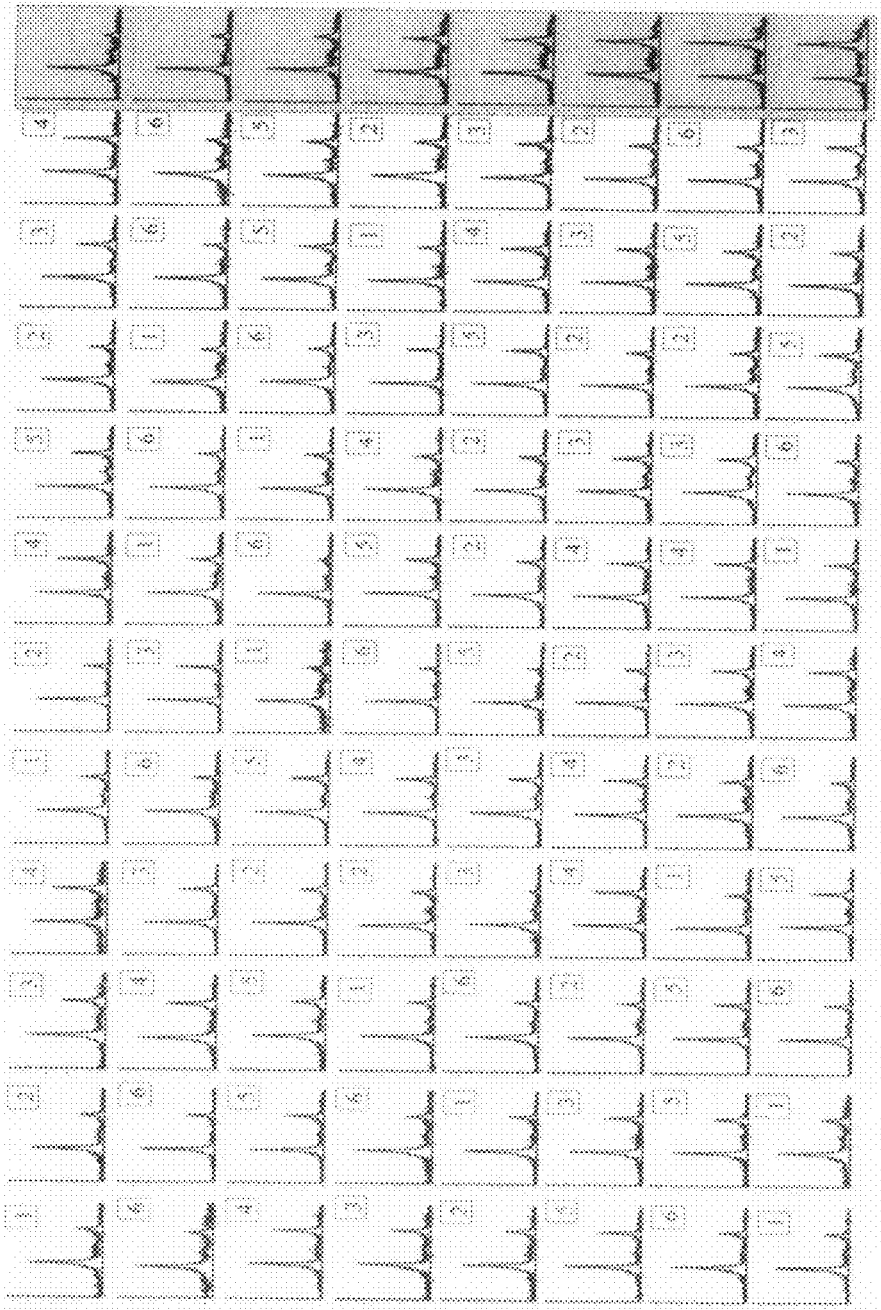
FIG. 10 is an illustration of a high-throughput quantitative analysis of $\beta_2$m from human plasma samples using the integrated system and methods described in this invention.

Another demonstration of the integrated system and methods described within the present invention comes from FIG. 10 high-throughput quantitative analysis of $\beta_2$m from human blood. The plasma samples from six individuals were prepared as described in FIG. 8. Eighty-eight wells of the 96-well sample plate received 15 μL plasma aliquots (the samples from the six individuals were randomized on the 96-well plate), 7.5 μL of equine plasma (undiluted) and 128 μL of HBS buffer. A series of dilutions of a $7.6 \times 10^{-4}$ mg/mL standard solution of purified human $\beta_2$m were prepared (spanning a concentration range of $7.6 \times 10^{-4}$ to $1.14 \times 10^{-4}$ mg/mL) and used as samples (15 μL of each) in the last column (8 wells) on the 96-well plate. Parallel sampling processing and MALDI-TOF MS analysis was performed as described for FIG. 8, using the polyclonal anti-$\beta_2$m microcolumns. The mass spectra resulting from the high-throughput analysis of the 88 samples and the 8 standards are shown in this figure. Spectra taken from the standard samples are shaded.

Figures 11A, 11B:
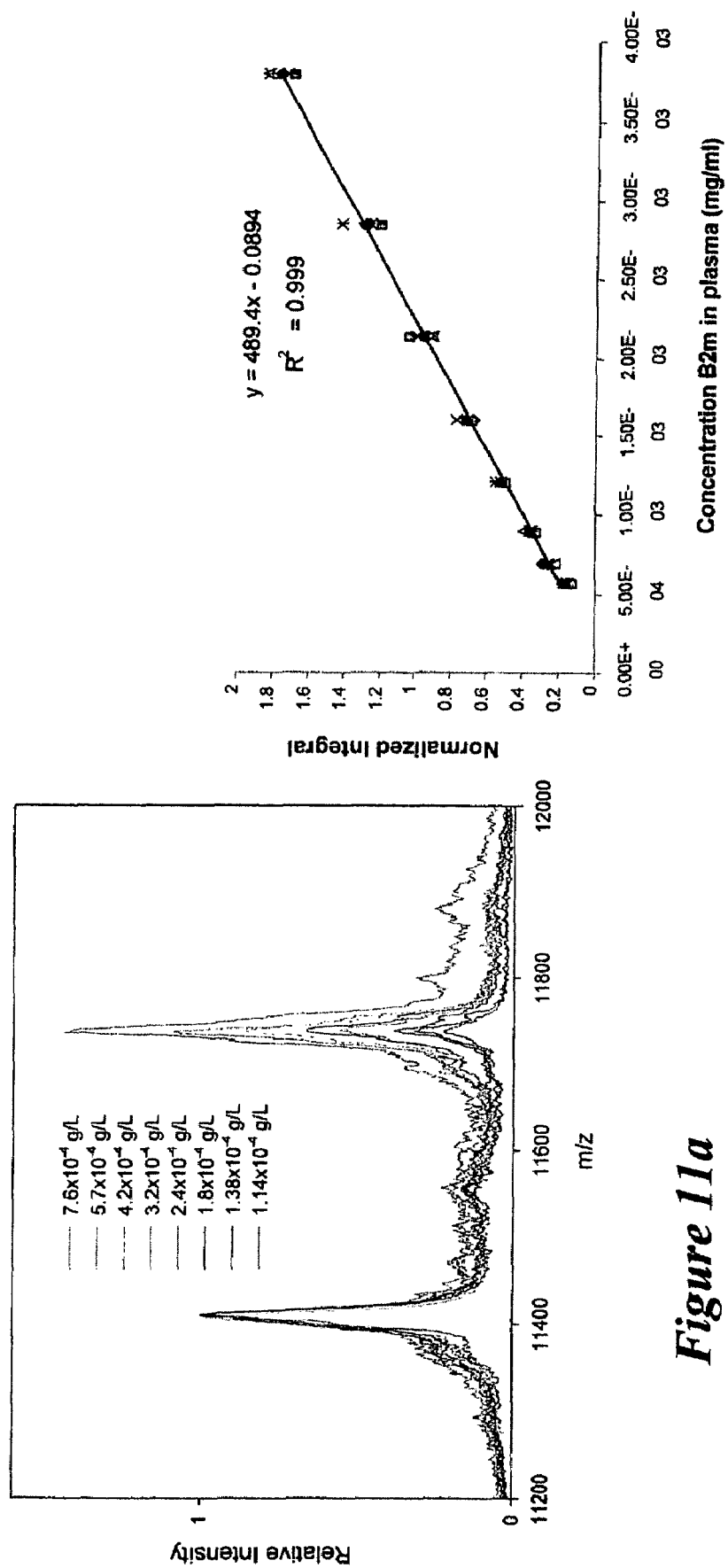
FIG. 11a and 11b illustrate the construction of a calibration curve from the data for the standard samples shown in FIG. 10 and for the purpose of determining the $\beta_2$m concentrations in the human plasma samples screened via the high-throughput analysis using the integrated system and methods described in this invention.

FIG. 11b is the calibration curve constructed from the FIG. 11a data for the standard samples shown in FIG. 10. The calibration curve is presented for the purpose of determining the $\beta_2$m concentrations in the human plasma samples screened via the high-throughput analysis using the integrated system and methods described in the present invention. Representative spectra of the data for each standard used to generate the working curve are presented overlain in FIG. 11a. Each spectrum was normalized to the equine $\beta_2$m signal through baseline integration, and normalized integrals for the human $\beta_2$m signals determined. Integrals from five spectra taken for each calibration standard were averaged and the standard deviation calculated. A calibration (standard) curve was constructed by plotting the average of the normalized integrals for each standard vs. the human $\beta_2$m concentration in the standard sample (adjusted for the human plasma dilution factor). The working curve generated is shown in FIG. 11b. The concentration range was spanned with good linearity ($R^2=0.999$) with overall standard deviation of the line of <2%.

Figure 12:
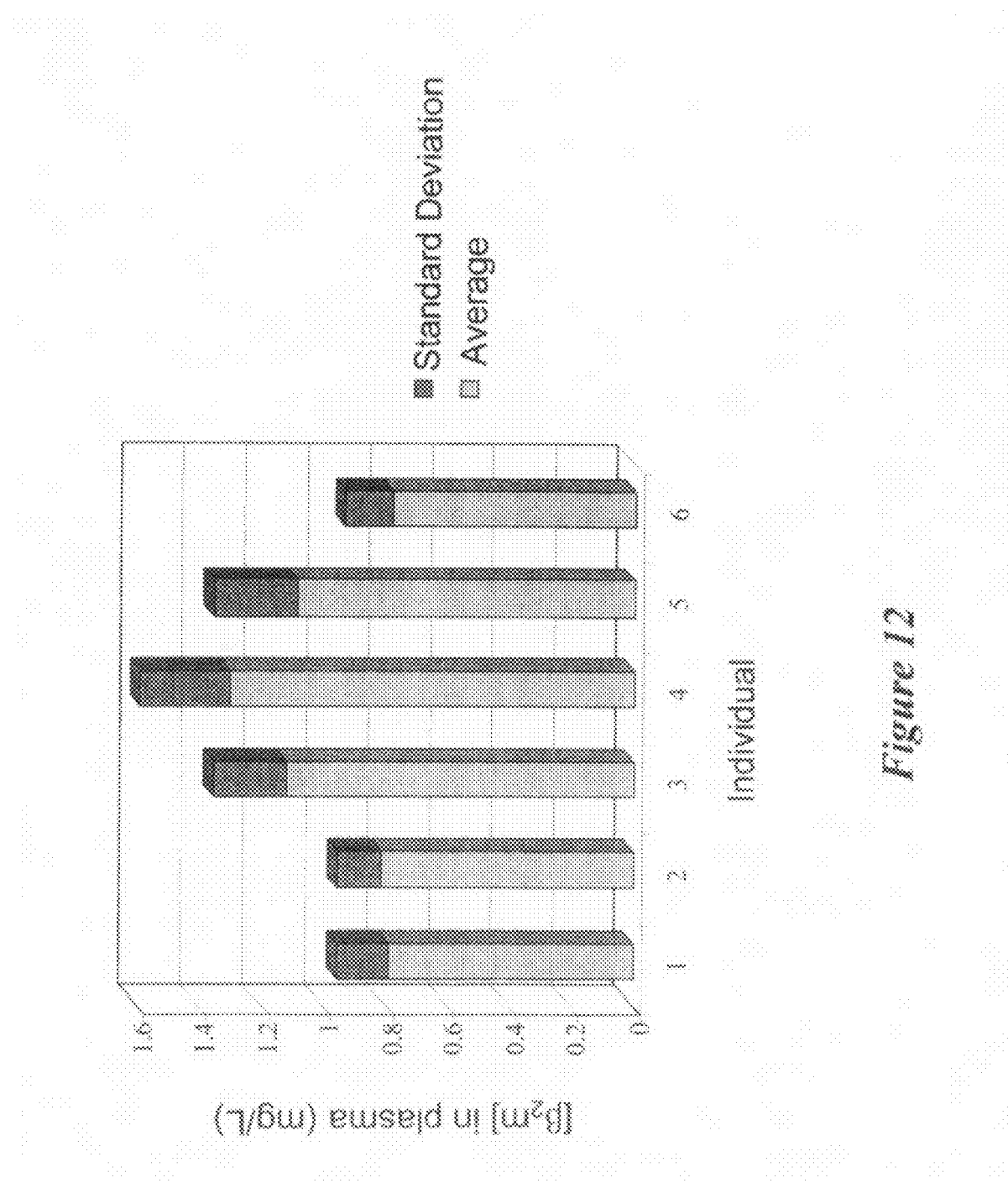
FIG. 12 shows bar analysis of the data shown above using the standard curve constructed above. Each spectrum for the 88 samples in FIG. 10 was normalized to the equine $\beta_2$m signal through baseline integration, and the normalized integral for the human $\beta_2$m signal determined. All human $\beta_2$m integrals for the same individual were averaged and the standard deviation calculated. The values of the averaged integrals were substituted in the equation derived from the standard curve, FIG. 11b, and the concentration of human $\beta_2$m was calculated for each individual. The range of concentrations determined was from 0.75 to 1.25 mg/L.

FIG. 12 is the bar analysis of the data shown in FIG. 10 using the standard curve constructed in FIG. 11b is illustrated. Each spectrum for the 88 samples from FIG. 10 was normalized to the equine $\beta_2$m signal through baseline integration, and the normalized integral for the human $\beta_2$m signal determined. The human $\beta_2$m integrals for the same individual were averaged and the standard deviation calculated. The values of the averaged integrals were substituted in the equation derived from the standard curve and the concentration of human $\beta_2$m was calculated for each individual. The range of concentrations determined was from 0.75 to 1.25 mg/L.

Example 23

Figure 13:
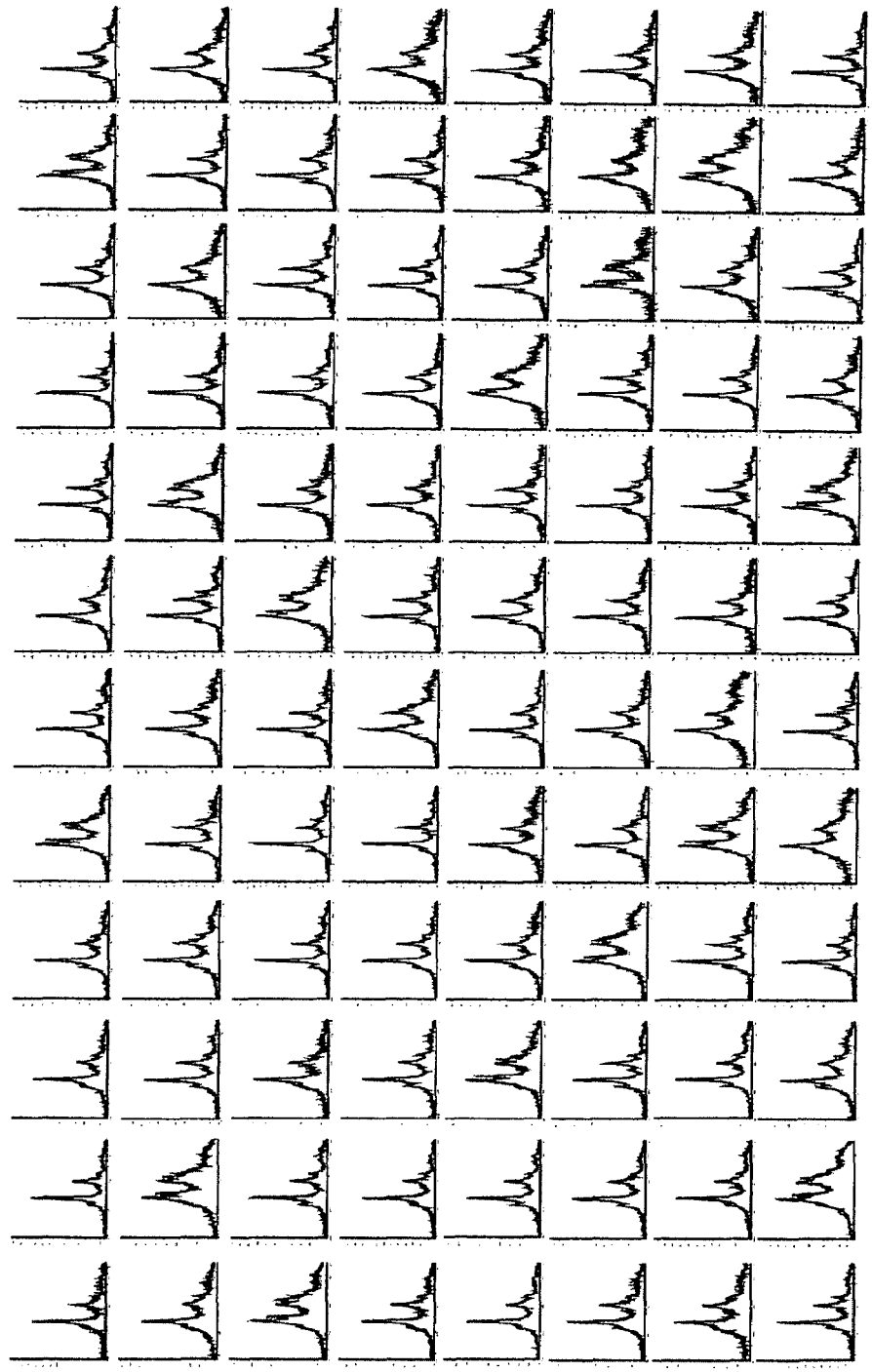
FIG. 13 is an illustration of a qualitative high-throughput screening of transthyretin (TTR) for posttranslational modification (PTM) and point mutations (PM) using the integrated system and methods described in this invention.

Integrated Combined System Approach Incorporating High Throughput Affinity Retrieval with Bioreactive Array MALDI-TOF Analysis for Point Mutations FIG. 13 is the qualitative high-throughput screening of transthyretin (TTR) for posttranslational modification (PTM) and point mutations (PM) was performed using the integrated system and methods described herein. Aliquots of diluted (5-fold) human plasma samples collected from six individuals were prepared for parallel screening on a 96-well plate. Each well received a 15 μL plasma aliquot (the samples from the six individuals were randomized on the 96-well plate), and 135 μL of BBS buffer. Parallel sampling processing entailed simultaneous incubation/capture of the 96 samples on 96 anti-TTR derivatized microcolumns. The polyclonal anti-TTR microcolumns were made via glutaraldehyde-mediated coupling of the antibodies to amino-coated/modified microcolumns. Captured proteins were eluted from the microcolumn array with a small volume of MALDI matrix (saturated ACCA solution) and stamped onto a MALDI target array surface comprised of self-assembled monolayers (SAM) chemically masked to make hydrophilic/hydrophobic contrast targets. Each sample spot on the target array was analyzed using mass spectrometry and the relative TTR abundance determined by an automated MALDI-TOF mass spectrometric analysis software routine. The mass spectra resulting from the high-throughput analysis of the 96 samples are shown in FIG. 13. In all of the spectra, the TTR signal is accompanied by another signal at higher mass, indicating posttranslationally processed TTR form. In addition, all spectra resulting from the analysis of one plasma sample showed two additional signals at masses ~30 Da higher than the two "original" TTR signal. See FIGS. 15 and 16 for identification of these peaks.

Figure 14:
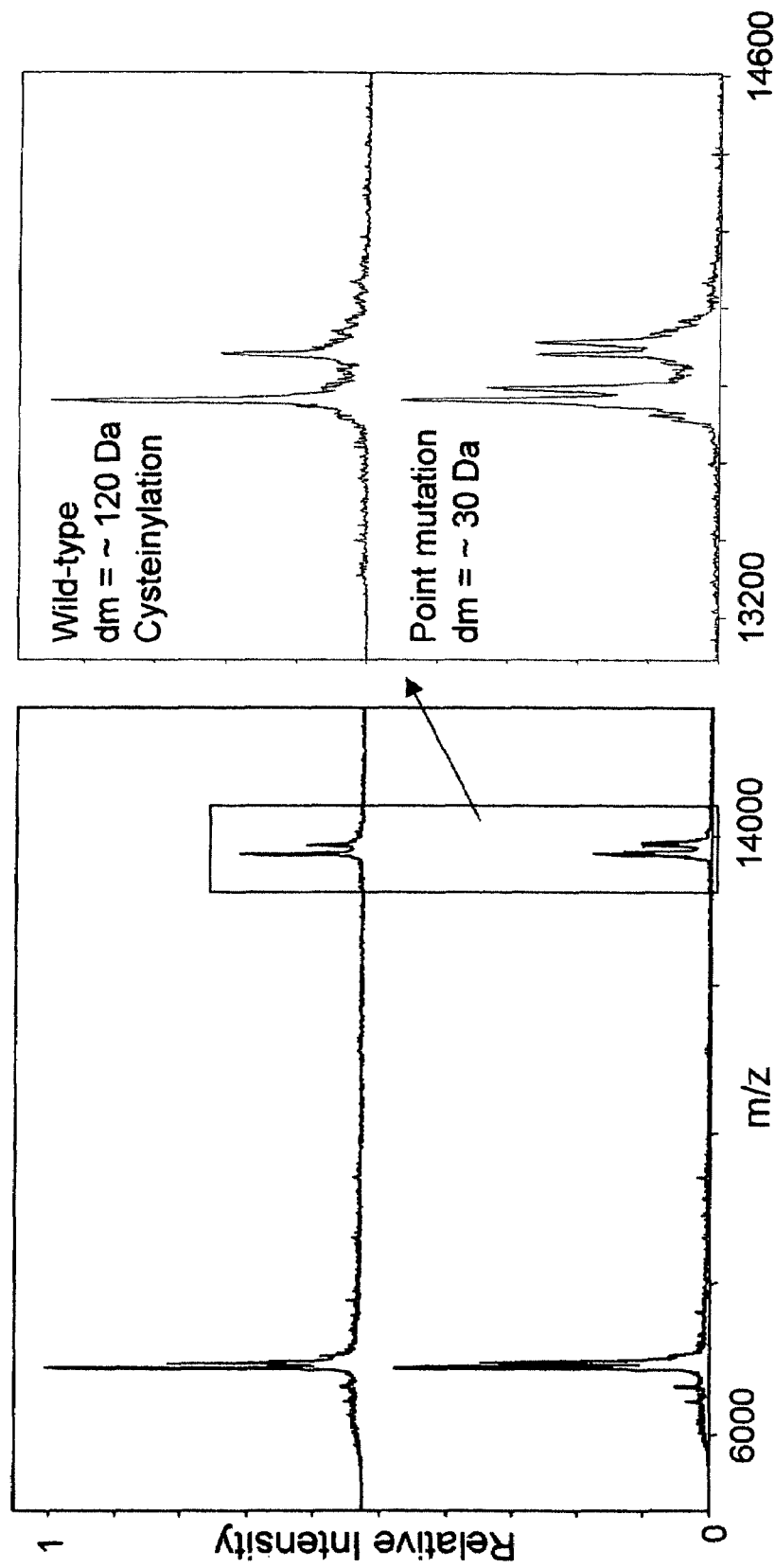
FIG. 14 illustrates identification of the posttranslational modifications and point mutations observed in the high-throughput TTR analysis using the integrated system and methods described in this invention.

FIG. 14 is the identification of the posttranslational modifications and point mutations observed in the high-throughput TTR analysis was performed using the integrated system and methods described herein. Shown are representative spectra resulting from analysis of samples from two individuals, showing the existence of two and four TTR signals, respectively. In the upper spectrum, two signals attributable to TTR are observed. The signals correspond well to the theoretically calculated mass of TTR ($MW_{TTR}=13,762$) and that of an oxidized TTR variant ($TTR_{ox}$) resulting from cysteinylation at Cys10 (introducing a mass shift of +119 Da). In the lower spectrum, in addition to the above-mentioned two TTR signals, two additional peaks at masses ~30 Da higher than the two "original" TTR signal are observed. See FIGS. 15 and 16 for identification of these two peaks.

Figure 15:
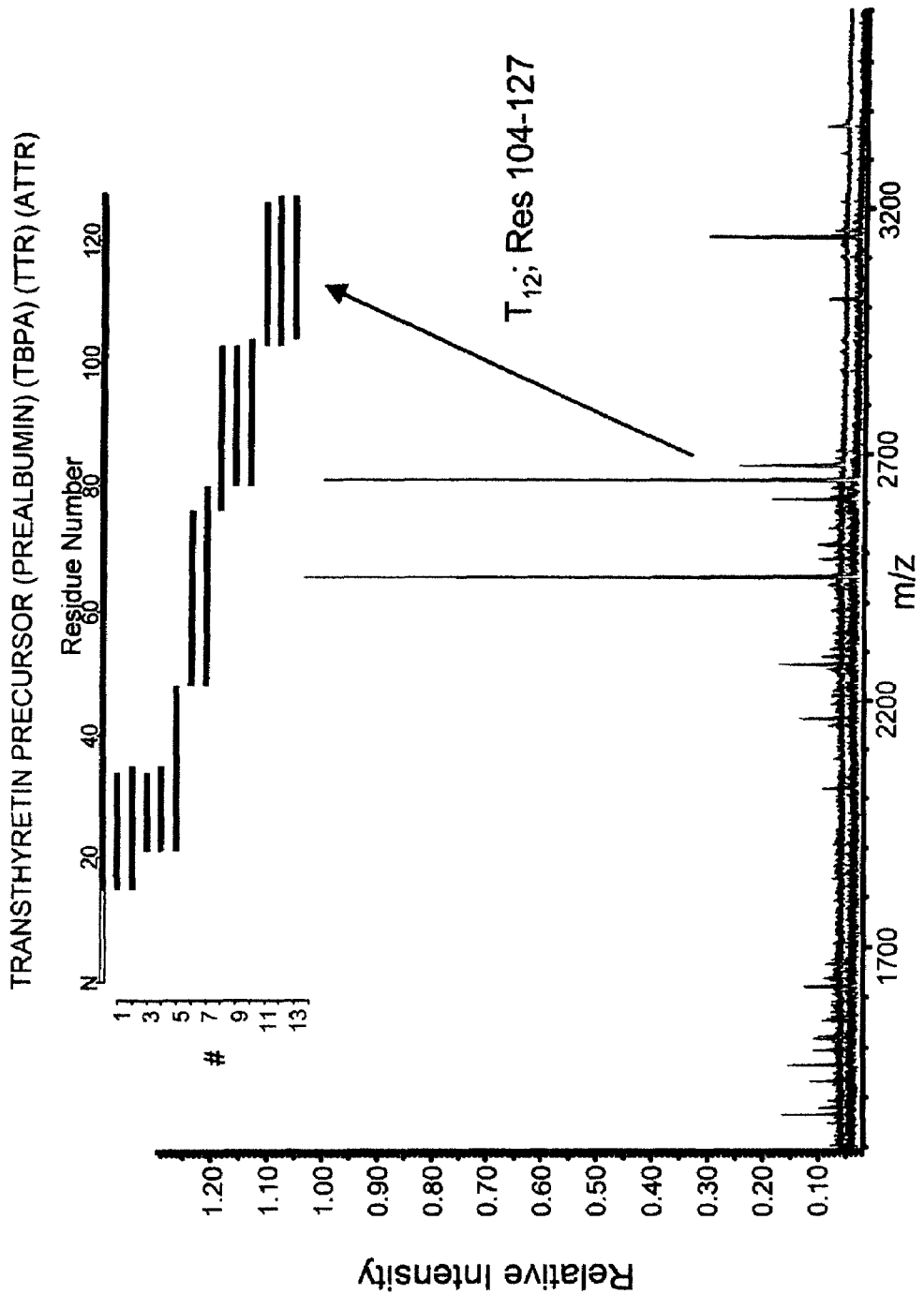
FIG. 15 illustrates the identification of point mutation via incorporation of derivatized mass spectrometer target platforms in the system and methods described in this invention.

Continued analysis of the TTR point mutation, displayed in FIG. 15, is illustrated using combined high-throughput affinity retrieval in concert with derivatized mass spectrometer target array in the system platform and the methods described in the present invention. The samples used were the same ones utilized for FIG. 14. TTR from diluted (50-fold, in HBS) human plasma was captured via polyclonal anti-TTR microcolumns, as described for FIG. 13. Instead of matrix elution, the captured proteins were eluted with a small volume of 10 mM HCl onto trypsin-conjugated targets containing buffered target spots (50 mM TRIS buffer pH 9.5) for sample pH modulation (buffer exchange). Shown in this figure are mass spectra resulting from a twenty-minute trypsin digest done at 40° C. of the proteins eluted from the anti-TTR microcolumns. The resulting two tryptic peptide maps localize the mutation in the tryptic fragment-12 ($T_{12}$), containing residues 104-127. A database search points to two possible TTR mutations in this region of the sequence: Ala109→Thr [DNA base change GCC→ACC], $\Delta m=30.011$ Da, and Thr 119→Met [DNA base change ACG_ATG], $\Delta m=29.992$ Da. The identification of the correct mutation is shown in FIG. 16.

Figure 16:
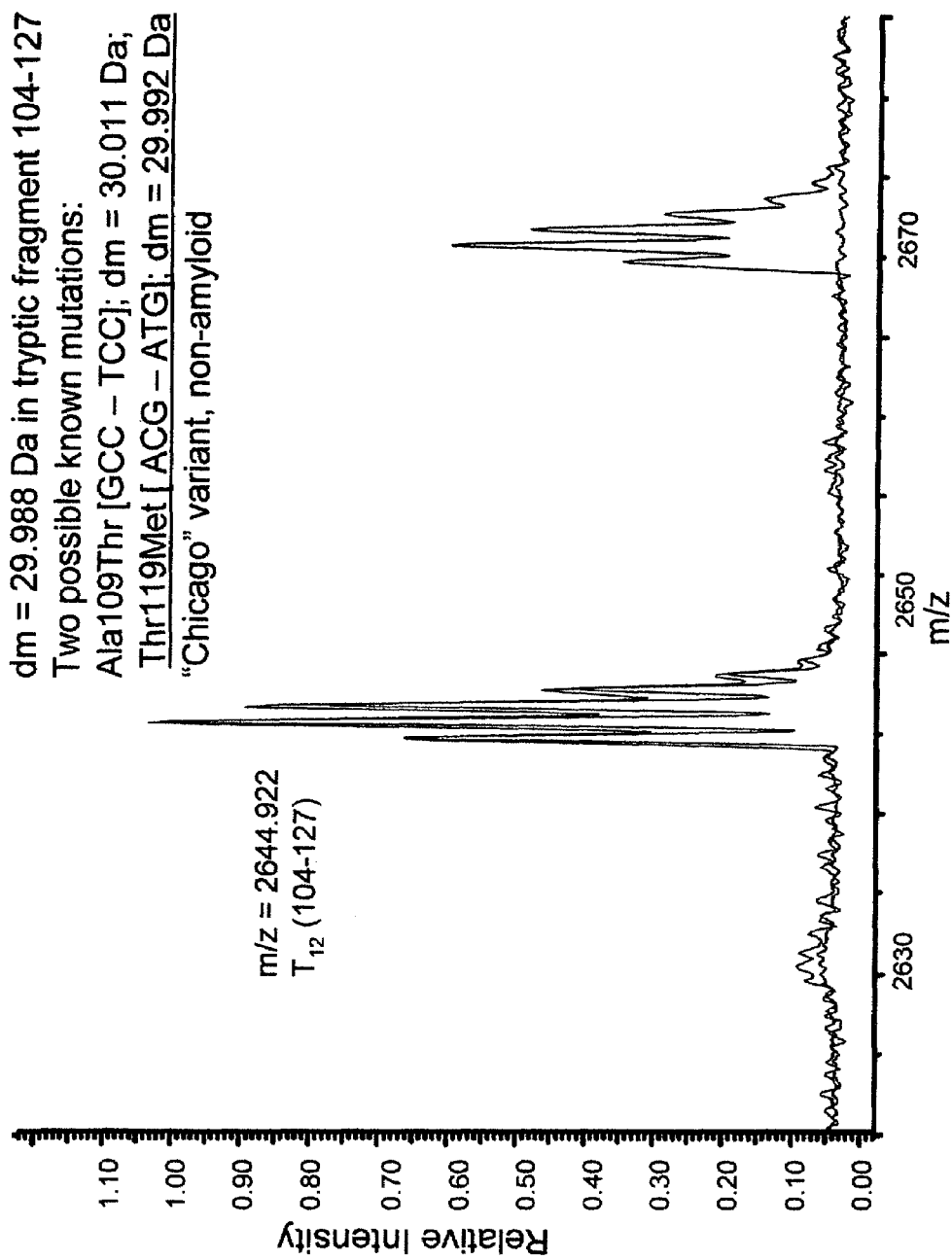
FIG. 16 illustrates the use of a high-resolution reflectron mass spectrometry as part of the integrated system and methods described in this invention in determining the identity of the point mutations detected in the analysis of the plasma samples shown in FIG. 15.

FIG. 16 is the high-resolution reflectron mass spectrometry used in determining the identity of the point mutations detected in the analysis of the plasma samples shown in FIG. 15 forming an integral part of the integrated system and methods described in the present invention. The monoisotopic signal for the tryptic digest fragment $T_{12}(104-127)$ in normal (native) TTR shows at m/z=2644.922, denoting $\Delta m=29.988$ Da difference with the monoisotopic signal for the mutant TTR. Accordingly, the point mutations is assigned to Thr 119→Met, $\Delta m=29.992$ Da. This TTR point mutation results in a so-called "Chicago prealbumin" variant, a nonamyloid mutation. The results shown in FIGS. 13, 14, 15, and 16 in combination illustrate the use of the system and the methods described herein in identifying posttranslational modifications and point mutations via concerted high-throughput screening analyses of biological samples.

Example 24

Integrated Combined System Approach Incorporating High Throughput Affinity Retrieval with Bioreactive Array MALDI-TOF for Analysis of Posttranslational Modification (PTM)

Figure 17:
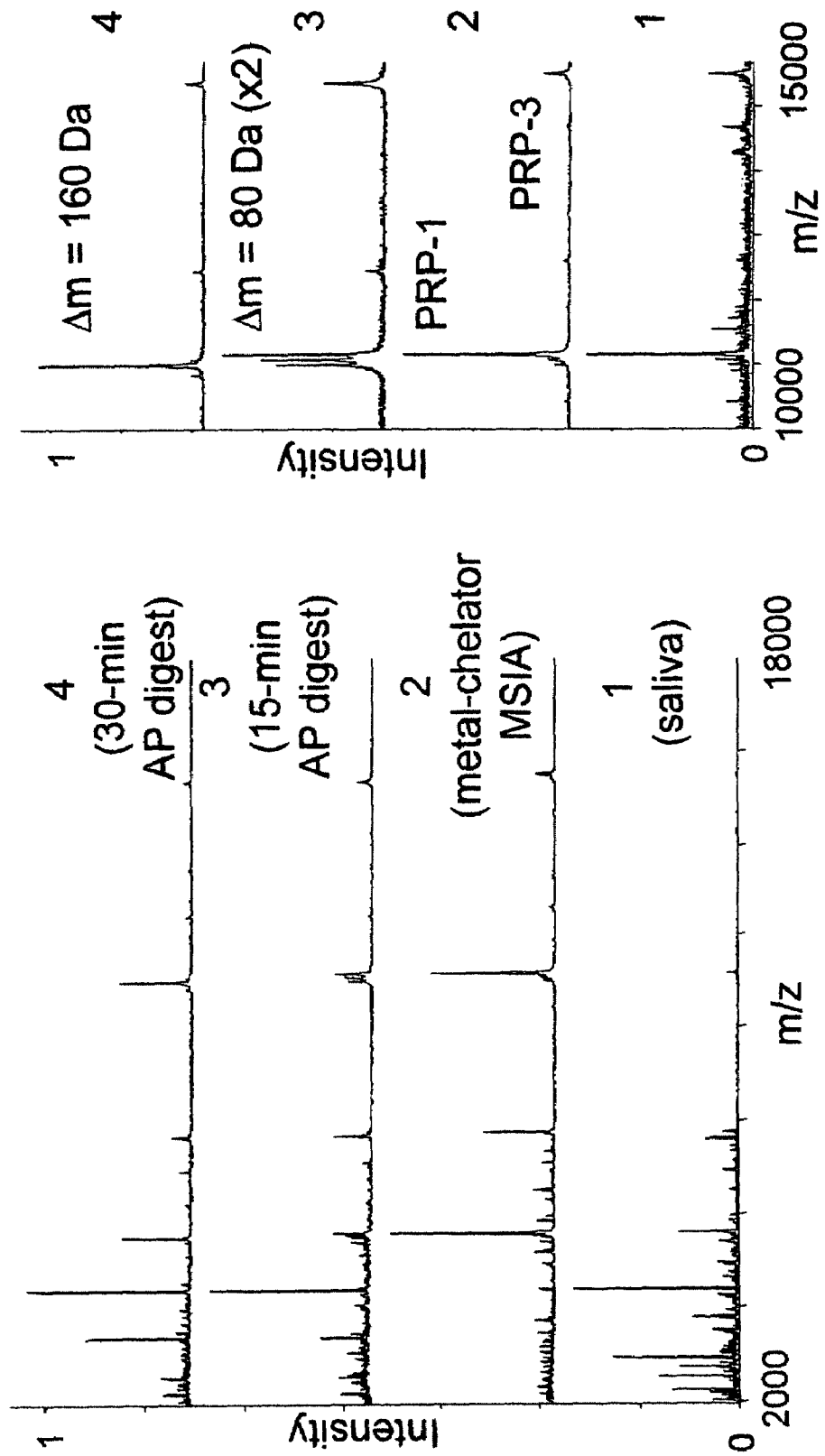
FIG. 17a Concerted biofluid phosphate analysis-chelator affinity pipettes with alkaline phosphatase functionalized target array. (1) Human whole saliva (10 µL diluted 10 fold), (2) sample in (1) through EDTA/Ca$^{2+}$ affinity pipettes, (3) sample in (2) eluted via 10 mM HCl addition and stamped onto AP-BRP incorporating 50 mM borate buffer pH=10 buffer exchange and fifteen minute phosphate digest (50° C.), (4) sample in (3) with extended thirty minute digest. Direct analysis of ten by dilution of human saliva significantly lacks proline rich protein-1 (PRP-1), the serine modified phosphate rich protein of interest.
FIG. 17b Spectrum in (2) shows EDTA/$Ca^{2+}$ affinity pipette capture of two phosphate rich proteins, PRP-1 and PRP-3. Mass signature of dephosphorylation is evident in spectral trace (3) and complete in (4). Illustrating multi-analyte detection accompanied by partial and complete dephosphorylation of phospho-proteins captured/digested out of biological fluid for post-translational analysis (i.e., phosphorylation events.

FIG. 17a is representative of the qualitative high-throughput screening for posttranslational modifications present in biological fluid performed using the integrated system and methods described herein. Concerted biological fluid phosphate analysis was performed using chelator affinity pipettes in conjunction with alkaline phosphatase (AP) functionalized target array. Here, chelator affinity pipettes were prepared as previously disclosed in accordance with example 14. Human whole saliva centrifuged and diluted 10 fold was either analyzed in sample or after incubation with metal chelator affinity pipettes. Captured analyte from metal chelator affinity pipettes was then eluted using dilute acid addition to disrupt the chelator/metal/analyte interaction and stamped onto a hydrophilic/hydrophobic contrast target array or alkaline phosphatase functionalized target array. The later incorporated buffer exchange for subsequent phosphate digests. Direct analysis of dilute human saliva significantly lacks proline rich protein-1 (PRP-1), the serine modified phosphate rich protein of interest. The FIG. 17b(2) spectrum denotes metal chelator affinity pipette capture shown as two phosphate rich proteins, PRP-1 and PRP-3. The dephosphorylation mass signature is evident in spectral trace FIG. 17b(3) and complete in FIG. 17b(4). Illustrating multi-analyte detection accompanied by partial and complete dephosphorylation of phospho-proteins captured/digested out of biological fluid for post-translational analysis, such as phosphorylation events.

Example 25

Figure 18:
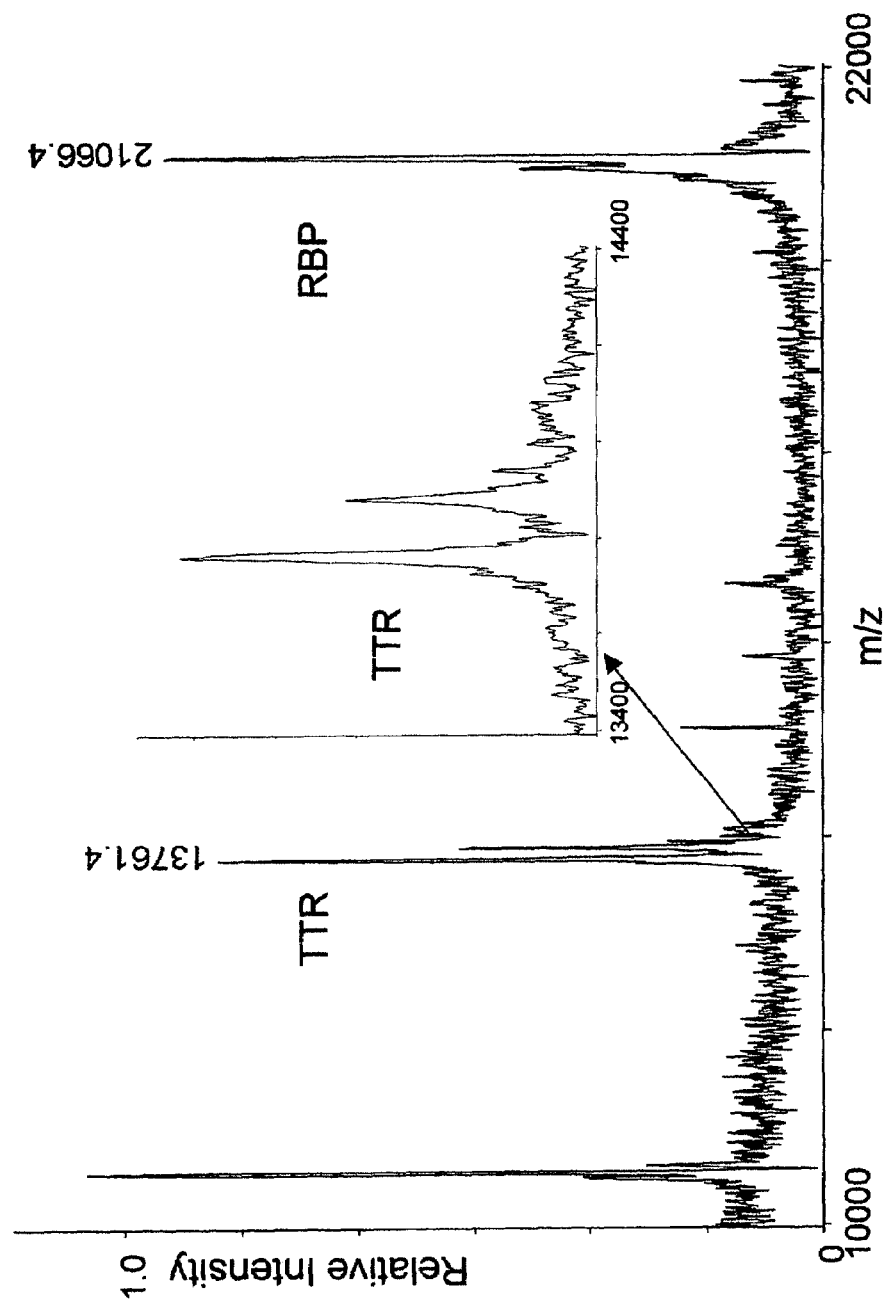
FIG. 18 MSIA delineation of multi-protein complex between retinol binding protein (RBP) and transthyretin (TTR). Polyclonal anti-RBP affinity pipettes were formed via glutaraldehyde mediated amine base support surface coupling. Human plasma was prepared and used as in FIG. 8. MSIA shows in vivo affinity retrieval of RBP (MW=21,062 Da) and complexed TTR (MW=13,760 Da). Illustrating protein interactions exiting in native protein complexes.

Integrated System Approach for Affinity Multi-Protein Interactions Integral in Nascentprotein Complex Retrieval with MALDI-TOF Analysis Illustrative in this example is the interaction within proteins that allow for retrieval of the native multi-protein complex present in biological media or biological samples. Demonstrated in FIG. 18 is the multi-protein complex between retinol binding protein (RBP) and transthyretin (TTR) from human plasma samples performed using the integrated system and methods of the present invention. Polyclonal anti-RBP affinity pipettes were formed using glutaraldehyde mediated amine base support surface coupling. Human plasma was prepared and used as previously described in above examples. MSIA delineates in vivo affinity retrieval of RBP and complexed TTR. The multi-protein complex between retinol binding protein (RBP) and transthyretin (TTR) illustrates protein interactions exiting in native protein complexes.

Example 26

Figure 19:
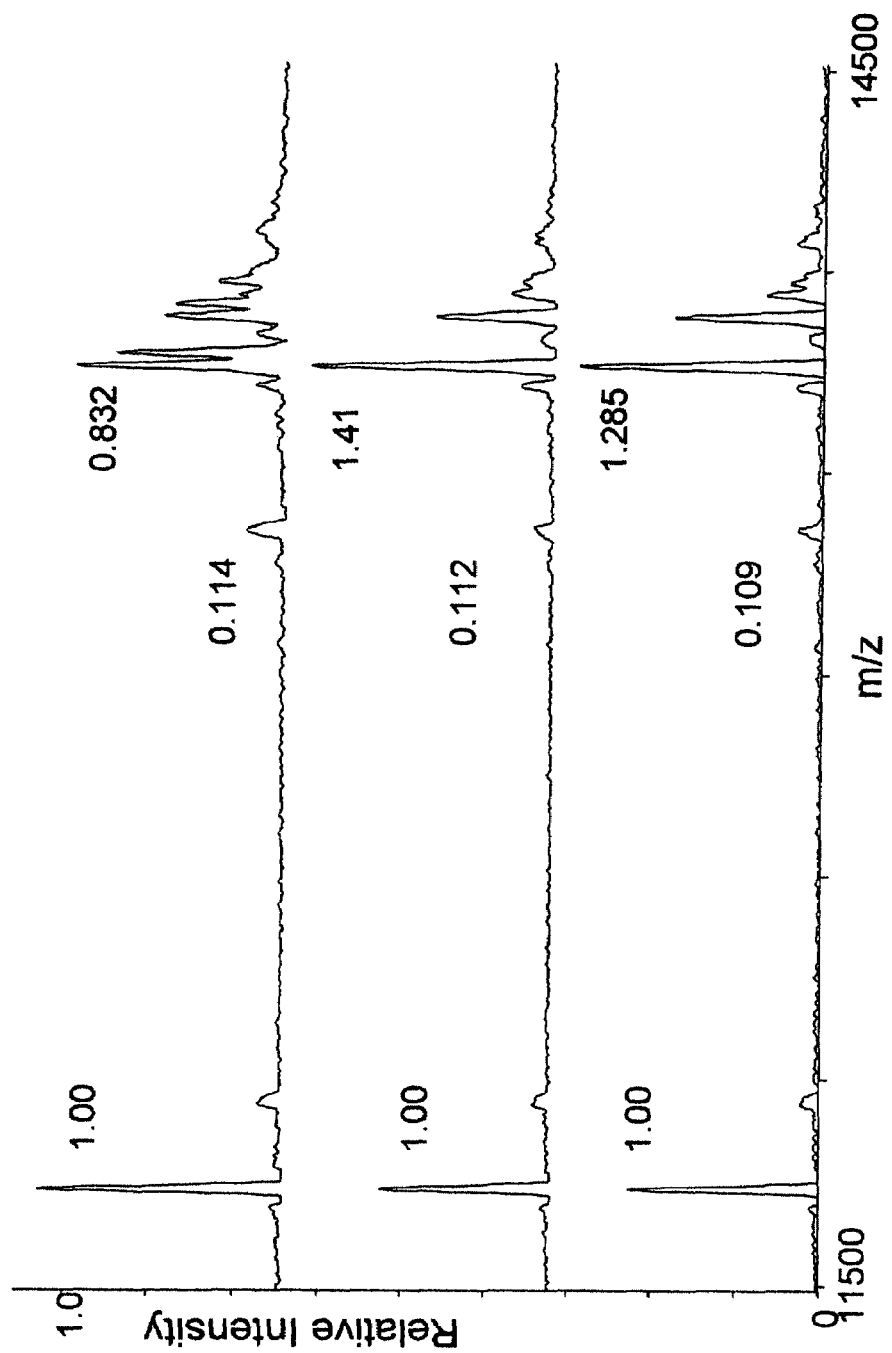
FIG. 19 Simultaneous rapid monitoring of multi-analytes for relative abundance. Amine activated, polyclonal anti-$\beta_2$m/CysC/TTR affinity pipettes are used to rapidly capture their respective analytes out of human plasma (50 fold diluted in HBS). The figure illustrates one of the uses for multi-antibody affinity pipettes to $\beta_2$m, CysC and TTR to rapidly monitor for biological fluid level modulation and to quantify a modulated protein event from their normalized relative abundance. The figure illustrates one of the uses of affinity pipettes for monitoring potential $\beta_2$m/CysC levels in acute phase of viral infection (ca. AIDS) or fibril formation from $\beta_2$m or TTR.

Integrated System Approach Incorporating High Throughput Multi-Analyte Retrieval and MALDI-TOF Analysis Multi-receptor affinity microcolumn high-throughput approaches are described in this example to illustrate multi-analyte analysis from human plasma samples performed for rapid qualification and semi-quantitation using the integrated system and methods of the present invention. FIG. 19 shows simultaneous rapid monitoring of multi-analytes for relative abundance. Amine activated, polyclonal anti-b2m/CysC/TTR affinity pipettes were used to rapidly capture their respective analytes out of human plasma as previously described. This then illustrates one of the uses for multi-antibody affinity pipettes to $\beta_2$m, CysC and TTR to rapidly monitor for biological fluid level modulation and to quantify a modulated protein event from their normalized relative abundance. Further illustrating one of the uses of affinity pipettes in the integrated system and methods of the present invention for monitoring potential $\beta_2$m/CysC levels in acute phase of viral infection (ca. AIDS) or fibril formation from $\beta_2$m or TTR.

Figure 20:
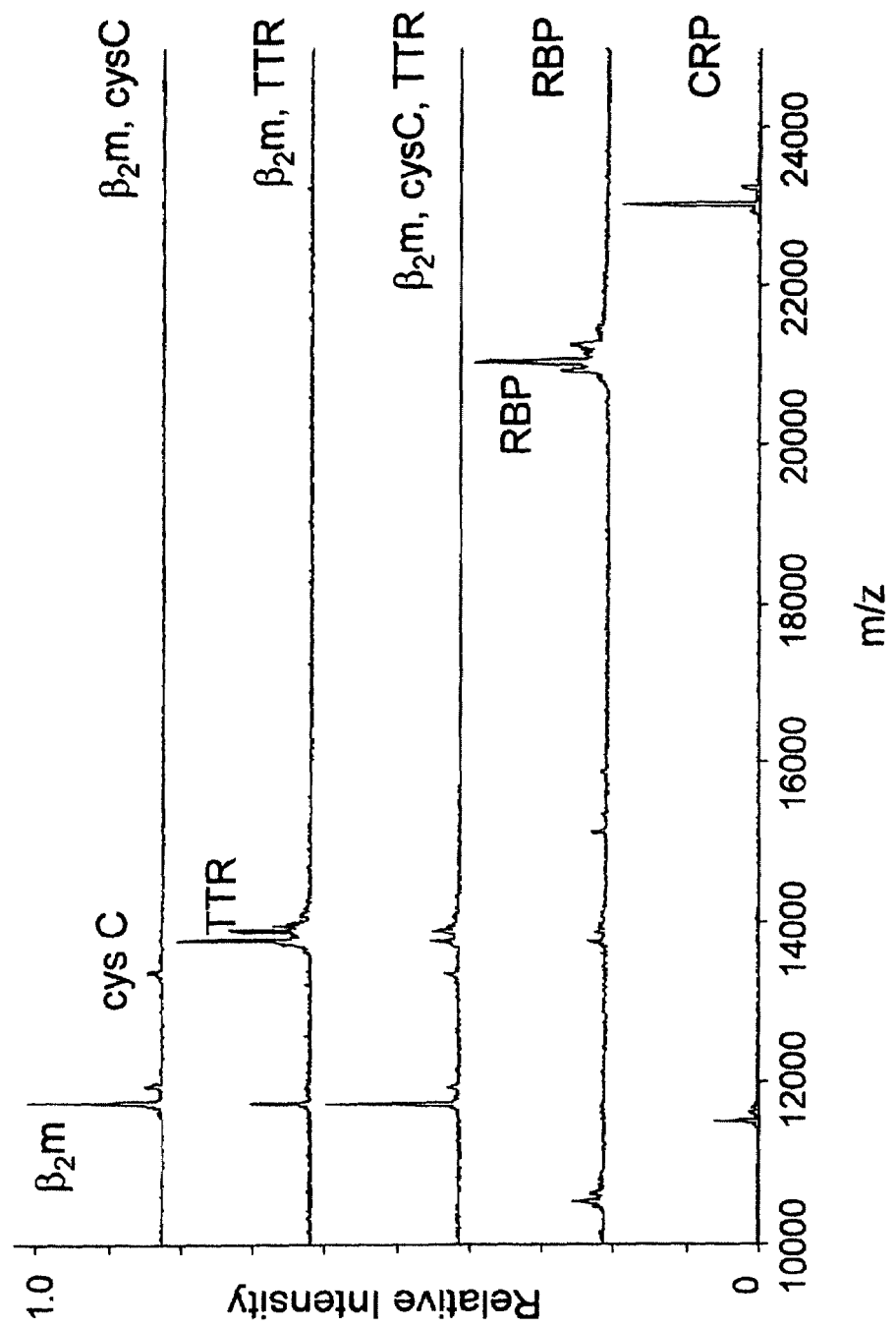
FIG. 20 Rapid monitoring of extended multi-analyte affinity pipettes. Combinations/individual polyclonal antibody affinity pipettes incorporating $\beta_2$m, TTR, RBP, Cystatin C or CRP capture respective analytes from human plasma (50 fold dilution in HBS). This figure illustrates one of the uses for multi/single-antibody affinity pipettes to $\beta_2$m, CysC, TTR or CRP to rapidly monitor for biological fluid level modulation and to potentially quantify a modulated protein event from their normalized relative abundance. This figure illustrates another of the uses of affinity pipettes for monitoring potential $\beta_2$m/CysC levels in acute phase of viral infection (ca. AIDS) or fibril formation from $\beta_2$m or TTR.
Figure 21:
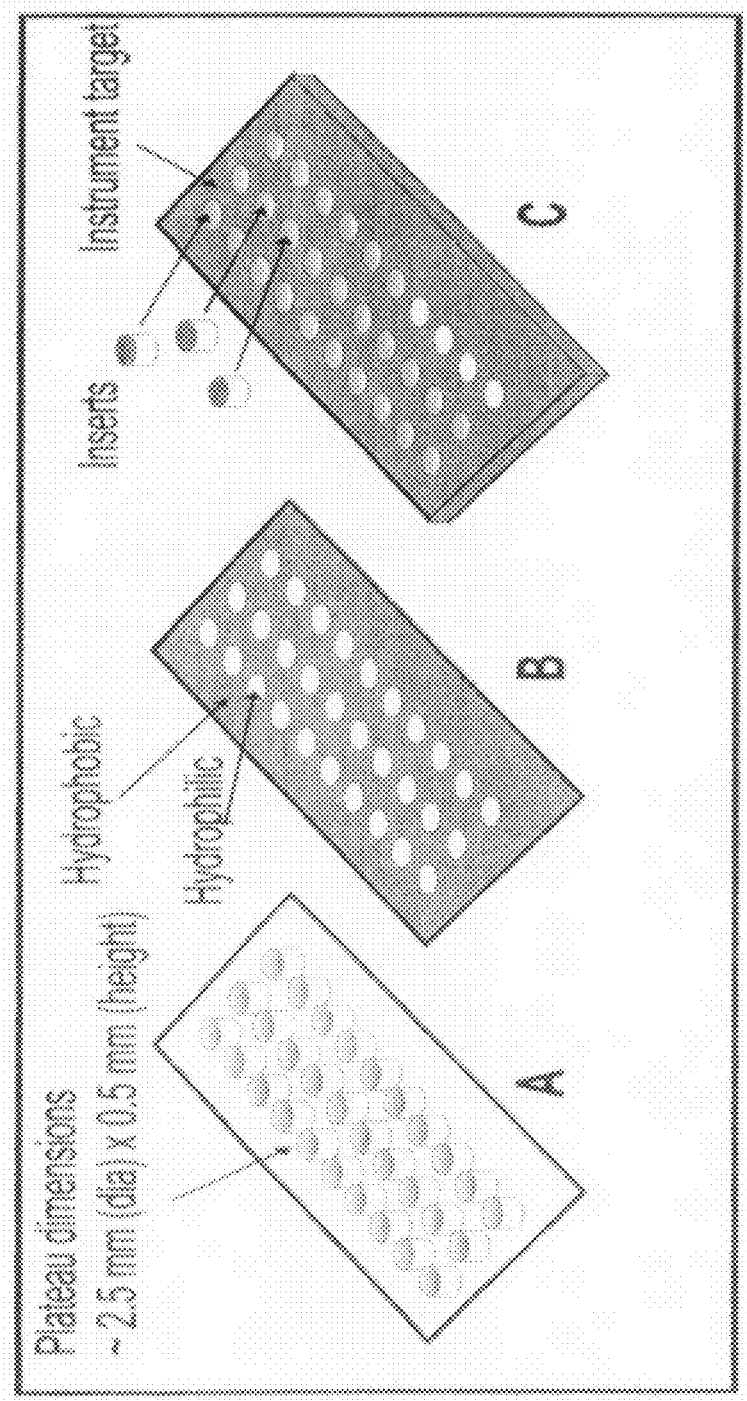
FIG. 21 Mass spectrometry target arrays. (A) Plateau target capable of confining sample through meniscus action. (B) Contrast design capable of confining sample through hydrophobic/hydrophilic action. (C) Insert targets for use with smaller sampling loads, expensive reagents, or sample transfers.

Shown in FIG. 20 is the rapid monitoring of extended multi-analyte affinity pipettes in the integrated system and methods of the present invention. Combinations as well as individual polyclonal antibody affinity pipettes incorporating $\beta_2$m, TTR, RBP, Cystatin C or CRP were used to capture respective analytes from human plasma (attained as previously stated in earlier examples). Illustrating another use for multi/single-antibody affinity pipettes to $\beta_2$m, CysC, TTR or CRP to rapidly monitor for biological fluid level modulation and to potentially quantify a modulated protein event from their normalized relative abundance. And further illustrates another of the uses of affinity pipettes for monitoring potential $\beta_2$m/CysC levels in acute phase of viral infection (ca. AIDS) or fibril formation from $\beta_2$m or TTR.

Given the ability to increase sample throughput, the integration of a high throughput system for mass spectrometric analysis of biomolecules finds increased use in large-scale clinical, diagnostic, and therapeutic efficacy, applications where exceptional qualitative and quantitative accuracy are both needed in biologically important biomolecule analysis out of biological fluids.

As used herein, "affinity microcolumn" refers to a molecular trap contained within a housing.

As used herein, "affinity reagent" refers to a chemical species on the surface of the molecular trap and is chemically activated, or activatable, and to which affinity receptors may be covalently linked.

As used herein, "affinity receptors" refers to atomic or molecular species having an affinity towards analytes present in biological media or biological samples. Affinity receptors may be organic, inorganic or biological by nature, and can exhibit broad (targeting numerous analytes) to narrow (target a single analyte) specificity. Examples of affinity receptors include, but are not limited to, antibodies, antibody fragments, synthetic paratopes, peptides, polypeptides, enzymes, proteins, multi-subunit protein receptors, mimics, organic molecules, polymers, inorganic molecules, chelators, nucleic acids, aptamers, as well as the below stated receptors.

As used herein, "analyte" refers to molecules of interest present in a biological sample. Analytes may be, but are not limited to, nucleic acids (DNA, RNA), peptides, hormonal peptides, hormones, polypeptides, proteins, protein complexes, carbohydrates or small inorganic or organic molecules having biological function. Analytes may naturally contain sequences, motifs or groups recognized by the affinity receptors or may have these recognition moieties introduced into them via processing such as cellular, extracellular, enzymatic, chemical, and the like.

As used herein, "biological media" or "biological sample" refers to a fluid or extract having a biological origin. Biological media may be, but are not limited to, cell extracts, nuclear extracts, cell lysates and excretions, blood, sera, plasma, urine, sputum, sinovial fluid, cerebral-spinal fluid, tears, feces, saliva, membrane extracts, and the like.

As used herein "chemically activate" refers to the process of exposing the affinity reagent to chemicals (or light) in order to subsequently attach (or photoactivate) tethering linkers and affinity receptors. Compounds able to activate affinity reagents may be, but are not limited to organic, inorganic, or biological reagents. Often, it is advantageous to activate the affinity reagent using multiple steps including the use of a tethering linker. As used herein, "tethering linker" refers to compounds intermediate to the affinity reagent and the affinity receptor that exhibit the desirable characteristics of being able to be derivatized with high densities of affinity receptor and showing low binding of non-specified compounds. The tethering linker may be intrinsically active or require activation for attachment. Suitable tethering compounds include but are not limited to homo/hetero functional organics, natural and synthetic polymers and biopolymers.

As used herein, "dead volume" refers to the void volume within the molecular trap. As used herein, "low dead volume" refers to the range of 1 nanoliter to 1 milliliter.

As used herein, "high flow properties" refers to a minimum flow rate of 1 microliter per minute. Higher flow rates are considered to fall within the definition of high flow properties.

As used herein, "mass spectrometer" or refers to a device able to volatilize/ionize analytes to form vapor-phase ions and determine their absolute or relative molecular masses. Suitable forms of volatilization/ionization are laser/light, thermal, electrical, atomized/sprayed and the like or combinations thereof. Suitable forms of mass spectrometry include, but are not limited to, Matrix Assisted Laser Desorption/Time of Flight Mass Spectrometry (MALDI-TOF MS), electrospray (or nanospray) ionization (ESI) mass spectrometry, quadruple ion-trap, Fourier transform ion cyclotron resonance (FT-ICR), magnetic sector, or the like or combinations thereof mass analyzers.

As used herein, "mass spectrometer target" or "mass spectrometer target array" refers to an apparatus onto or into which one or more analytes are deposited for subsequent mass spectrometric analysis. Generally, targets will accommodate numerous samples and are of various geometrical configurations depending on the nature of the mass spectrometer for which they are designed. Suitable materials for constructing targets include metals, glasses, plastics, polymers, composites, and the like or combinations thereof.

As used herein "molecular trap" refers to a high surface area material having high flow properties and a low dead-volume, with affinity reagents bound to surfaces contained therein. The composition of the high surface area material may be, but is not limited to, crystal, glasses, plastics, polymers, metals or any combination of these materials. For example, these glasses may be silica glasses, borosilicates, sodium borosilicates, and other useful materials.

As used herein, the term "receptor" generally refers to one member of a pair of compounds that specifically recognize and bind to each other. The other member of the pair is termed a "ligand" and includes such things as complexes, protein-protein interactions, multianalyte analyses, and the like. Receptor/ligand pairing may include protein receptor (membranous), and its natural ligand (associated, or other proteins or small molecules). Receptor/ligand pairs may also include antibody/antigen, binding pairs, complementary nucleic acid, nucleic acid associating proteins and their nucleic acid ligands such as aptamers and their proteins, metal chelators and metal binding protein ligands, mimic dyes and their protein ligands, organic molecules and their interaction, such as hydrophobic patches, on or with biomolecules, ion exchangers and their electrostatic interaction on or with biomolecules, and the like.

As used herein, "robotics" refers to devices and procedures capable of the unattended processing of samples. Preferably, the robotics operate on numerous samples in parallel to maximize the number of samples processed and analyzed in a given amount of time.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration, and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. An affinity microcolumn comprising a high surface area material comprising a phase separable metal, which has high flow properties and a low dead volume, contained within a housing and affinity reagents bound to the surface of the high surface area material, wherein the affinity reagents are either activated or activatable and the high surface area is formed by thermal surface phase separation of the metal and leaching one of the separated soluble phases to result in a pore formation.

2. The affinity microcolumn according to claim 1 wherein the affinity reagents that are bound to the surface of the high surface material further comprise affinity receptors bound to the affinity reagents.

3. The affinity microcolumn according to claim 2 further comprising a tethering molecule that is activated or activatable and binds the affinity receptors to the affinity reagents.

4. The affinity microcolumn according to claim 2 further comprising an amplification media interposed between the affinity reagents and the affinity receptors, where the amplification media allows better access by an analyte to the affinity receptors than in the absence of the amplification media.

5. The affinity microcolumn according to claim 4 wherein the amplification media comprises at least one of a biological polymer, a non-biological polymer, and an inorganic polymer.

6. The affinity microcolumn of claim 1 wherein the housing is at least one of a micropipette or a manifold having more than one dimension.

7. The affinity microcolumn according to claim 1 further comprising an amplification media that is activated or activatable and is interposed between the affinity reagents and the affinity receptors, where the amplification media allows a high density of affinity receptors to be bound to the affinity reagents than in the absence of the amplification media.

8. The affinity microcolumn according to claim 7 wherein the amplification media comprises at least one of a biological polymer, a non-biological organic polymer, and an inorganic polymer.

9. The affinity microcolumn according to claim 1 wherein the high surface area material comprises porous metal.

10. The affinity microcolumn according to claim 9 wherein the porous metal comprises a porous metal molecular trap that is formed by molding.

* * * * *